(12) United States Patent
Guire et al.

(10) Patent No.: US 7,195,913 B2
(45) Date of Patent: *Mar. 27, 2007

(54) RANDOMLY ORDERED ARRAYS AND METHODS OF MAKING AND USING

(75) Inventors: Patrick E. Guire, Eden Prairie, MN (US); Kristin S. Taton, Little Canada, MN (US); John V. Wall, Woodbury, MN (US)

(73) Assignee: SurModics, Inc., Eden Praire, MN (US)

( * ) Notice: Subject to any disclaimer, the term of this patent is extended or adjusted under 35 U.S.C. 154(b) by 90 days.

This patent is subject to a terminal disclaimer.

(21) Appl. No.: 09/972,687

(22) Filed: Oct. 5, 2001

(65) Prior Publication Data

US 2003/0073086 A1 Apr. 17, 2003

(51) Int. Cl.
*C12N 5/02* (2006.01)
*C12M 33/00* (2006.01)

(52) U.S. Cl. .................. 435/401; 435/396; 435/395; 435/7.1; 435/4; 435/DIG. 15; 435/DIG. 14; 530/810; 530/811; 530/815; 530/816

(58) Field of Classification Search ............... 435/7.1, 435/4, 401, 396, 395, DIG. 15, DIG. 14; 530/815

See application file for complete search history.

(56) References Cited

U.S. PATENT DOCUMENTS

| 5,002,582 | A | 3/1991 | Guire et al. |
| 5,714,360 | A | 2/1998 | Swan et al. |
| 5,736,257 | A | 4/1998 | Conrad et al. |
| 5,900,481 | A | 5/1999 | Lough et al. |
| 6,133,436 | A | 10/2000 | Köster et al. |
| 6,429,027 | B1 * | 8/2002 | Chee et al. .................. 436/518 |

FOREIGN PATENT DOCUMENTS

| EP | 455 905 | 11/1991 |
| WO | WO 93/06925 | 4/1993 |
| WO | WO 99/18434 | 4/1999 |
| WO | WO 99/60373 | 11/1999 |
| WO | WO 99/67641 | 12/1999 |
| WO | WO 00/39587 | 7/2000 |
| WO | WO 00/48000 | 8/2000 |
| WO | WO 01/59432 | 8/2001 |

OTHER PUBLICATIONS

Arenkov et al, Analytical Biochemistry, 278, 123-131 (2000).*
Arshady, R. (1991) *Beaded polymer supports and gels I. Manufacturing techniques*, J. Chromatogr. 586:181.
Arshady, R. (1991) *Beaded polymer supports and gels II. Physicochemical criteria and functionalization*, J. Chromatogr. 586:199.
Ausubel, F.M., et al., ed. (1990) *Current Protocols in Molecular Biology*, Greene Pub. Associates and Wiley-Interscience, New York.
Chmura, A.J., et al. (2001) *Antibodies with infinite affinity*, Proc Natl Acad Sci, 98:8480.
Coligan, J.E., et al., eds. (1996) *Current Protocols in Protein Science*, John Wiley & Sons, New York.
Damha, M.J., et al. (1990) *An improved procedure for derivatization of controlled-pore glass beads for solid phase oligonucleotide synthesis*, Nucleic Acids Res. 18:3813.
Han, M., et al. (2001) *Quantum-dot-tagged microbeads for multiplexed optical coding of biomolecules* Nat Biotechnol 19:631.
Hayashi, T., et al. (1993) *Immobilization of Thiol proteases onto Porous Poly(vinyl alcohol) Beads*, Polymer Journal 25:489.
Lund, V., et al. (1988) *Assessment of methods for covalent binding of nucleic acids to magnetic beads, Dynabeads™, and the characteristics of the bound nucleic acids in hybridization reactions*, Nucleic Acid Res. 16:10861.
MacBeath, G., et al. (2000) *Printing Proteins as Microarrays for High-Throughput Function Determination*, Science 189:1760.
Michael, K.L., et al. (1998) *Randomly ordered addressable high-density optical sensor arrays*. Anal. Chem. 70:1242.
Pon, R.T., et al. (1988) *Derivatization of Controlled Pore Glass Beads for Solid Phase Oligonucleotide Synthesis*, BioTechniques 6:768.

* cited by examiner

*Primary Examiner*—T. D. Wessendorf
(74) *Attorney, Agent, or Firm*—Pauly, DeVries, Smith & Deffner, L.L.C.

(57) ABSTRACT

Arrays including microparticles having probe and marker moieties are used for the detection of a target in a sample. Microparticles are randomly immobilized on at least a portion of a substrate. A detection scheme is performed to detect the marker associated with the microparticle and the identity of the probe, and any target bound to the probe.

10 Claims, 7 Drawing Sheets

Figure 1
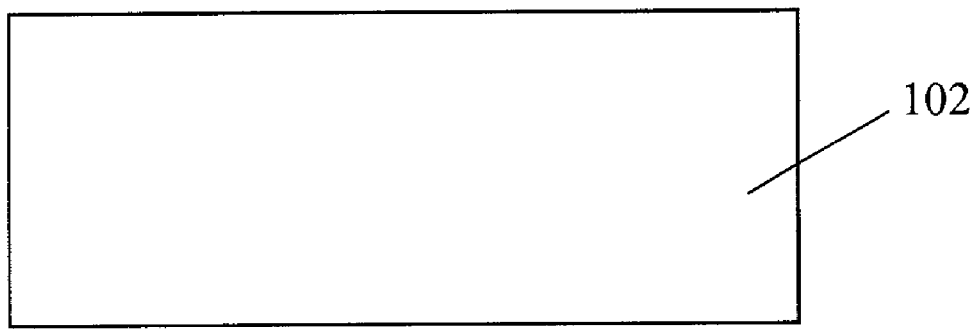
102
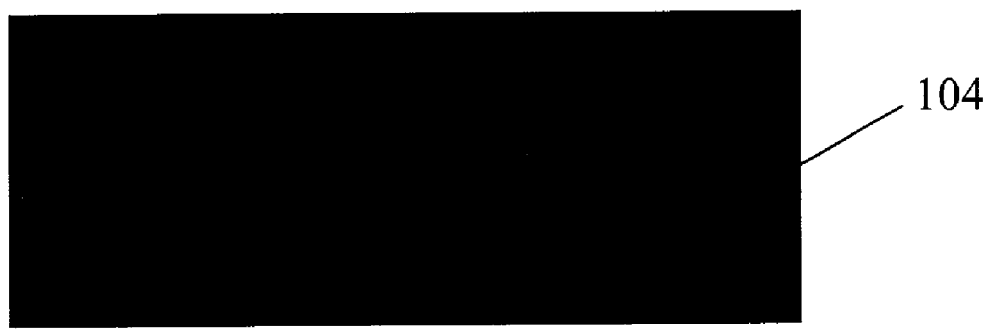
104
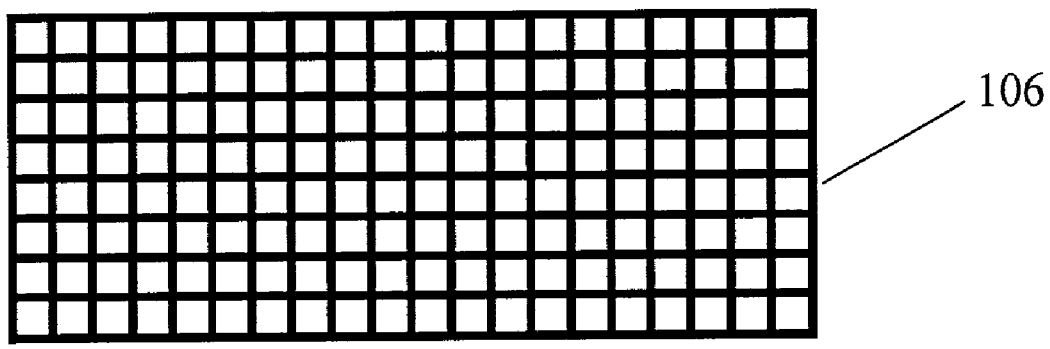
106
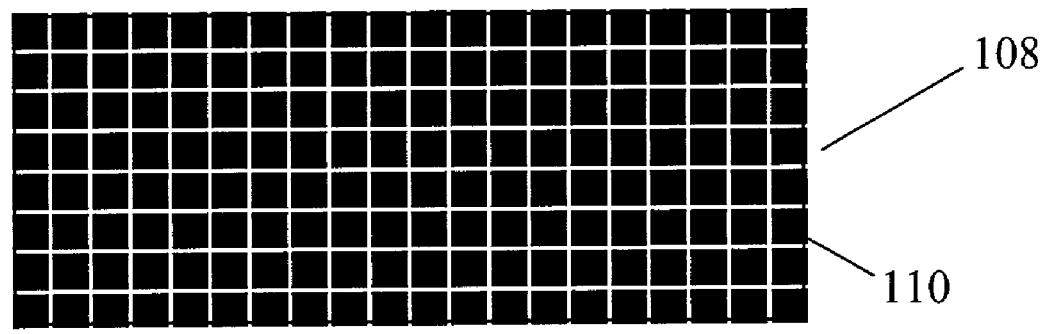
108
110

Figure 2
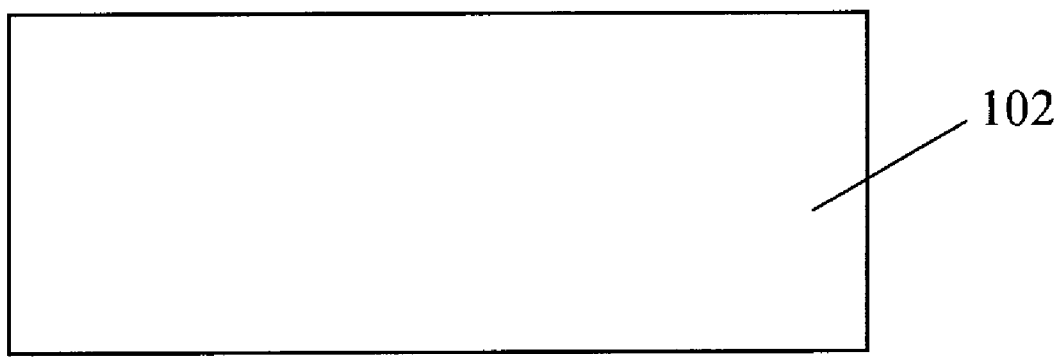
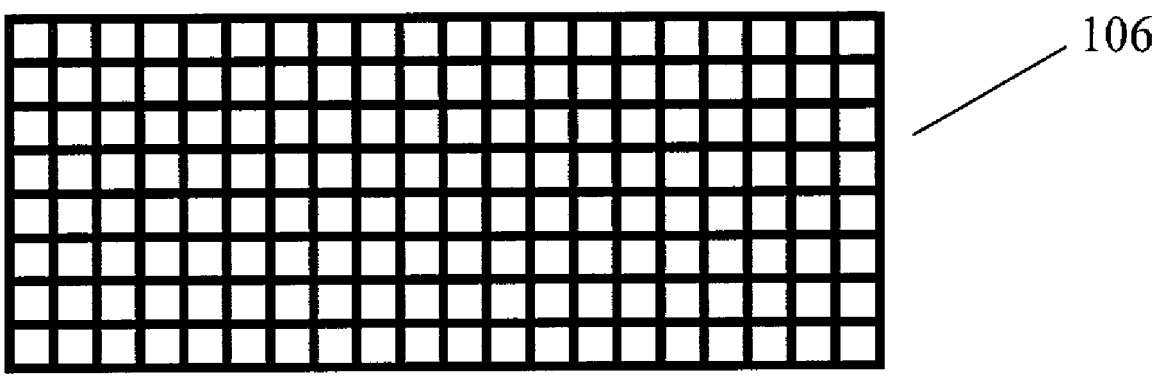
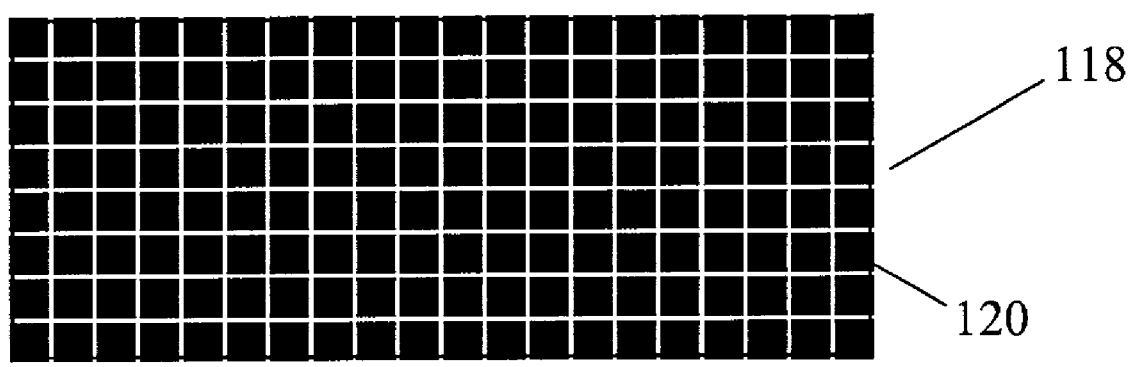

130  132  134            136

Figure 7
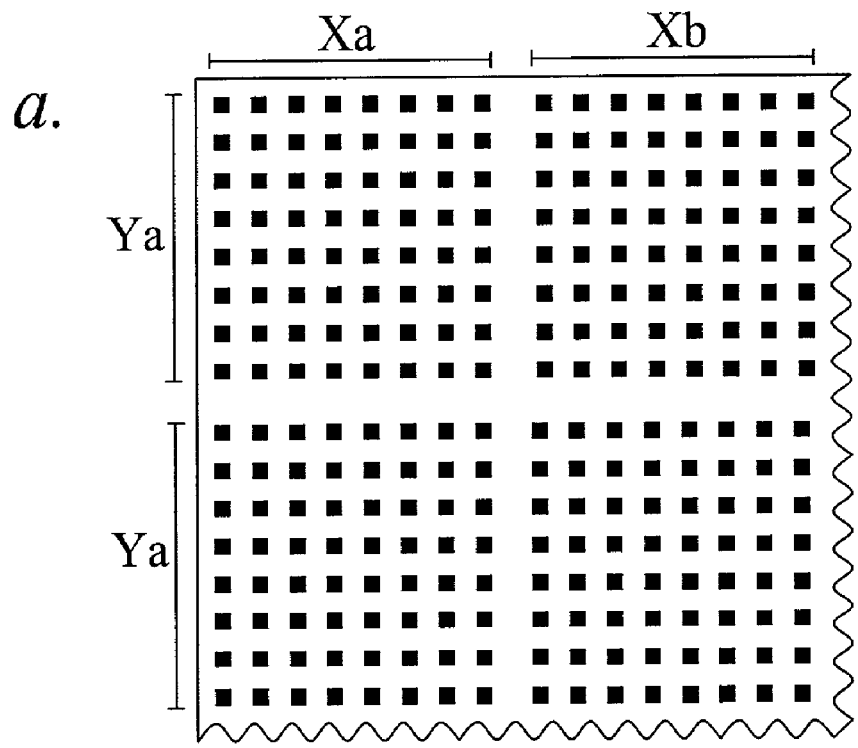
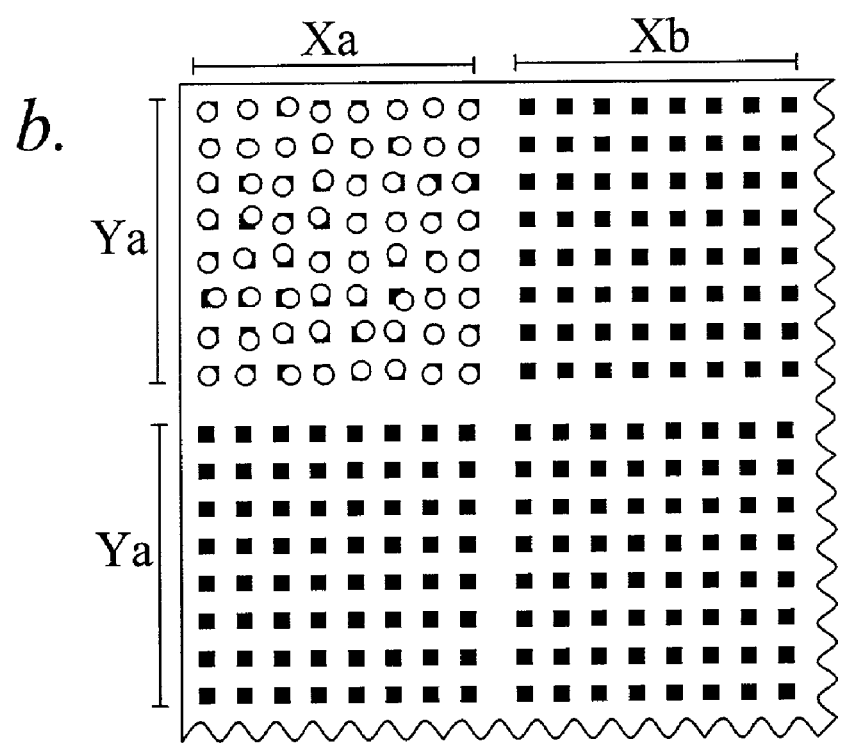

RANDOMLY ORDERED ARRAYS AND METHODS OF MAKING AND USING

FIELD OF THE INVENTION

This invention relates to the field of arrays for use in detecting a target suspected to be present in a sample. More particularly, the invention relates to arrays utilizing microparticles containing a self-encoding marker.

BACKGROUND OF THE INVENTION

In the past several years, a new technology, called the DNA array, has attracted interest among biologists. This technology promises to monitor part or all of an organism's genome on a single chip so that researchers can develop a better picture of the interactions among hundreds or thousands of genes simultaneously. This technology has been termed biochip, DNA chip, DNA microarray, gene array, and genome chip. Generally, a DNA array relies upon standard base pairing rules developed by Watson and Crick to analyze the presence, or the sequence, of a particular complementary nucleic acid sequence.

More recently, attention has focused on fabrication of protein or peptide arrays, and this area is commonly referred to as "proteomics." In one example of this approach, a library of peptides can be used as probes to screen for drugs. The peptides can be exposed to a receptor, and those probes that bind to the receptor can be identified. In one application, more than 10,000 protein spots were printed on a glass slide. The chip was used to identify protein-protein and protein-drug interactions (G. MacBeath and S. L. Schreiber, 2000, *Printing Proteins as Microarrays for High-Throughput Function Determination*, Science 189:1760–1763).

In more recent years, the demand for high-throughput and cost-effective analysis of complex mixtures has driven technology toward the fabrication of compact, high-density array devices. These arrays are fabricated using conventional techniques such as ink-jet printing, screen printing, photolithography, and photodeposition, in which the sensing chemistries are applied directly to the sensor surface. Typically, an array is fabricated by attaching a nucleic acid or peptide directly to a substrate. Multiple fabrication steps are commonly required that are labor intensive and subject to some degree of variability.

Given current fabrication schemes, the precise location of a probe on the surface of an array must be known prior to interrogating a sample. Therefore, fabrication of the arrays relies upon such techniques as printing or spotting of the probe onto the surface of the array, so that the addresses or locations of each probe is known prior to use of the array. Once the complexes are detected, the location of the complex is compared to the mapped surface of the array, and the identity of the target is determined.

SUMMARY OF THE INVENTION

The invention generally relates to detecting a target in a sample using an array of probes. More specifically, a target can be detecting using an array that includes a substrate and a plurality of microparticles, which are coupled to probes, randomly immobilized on the substrate. Each microparticle includes a probe and a self-encoding marker which forms a unique self-encoding marker/probe pair on the microparticle. The plurality of microparticles having unique self-encoding marker/probe pairs are immobilized on the substrate via an immobilization material. Detection of the target in a sample can be accomplished by applying a sample suspected of containing the target to the array, allowing the target to bind to the probes coupled to the microparticles, and then detecting a target marker coupled to the target and detecting the self encoding markers of microparticles having unique self-encoding marker/probe pairs. Although the microparticles are randomly located on at least a portion of the array, the presence and identity of the target can be determined by the self-encoding marker/probe pairs.

In some embodiments the immobilization material includes a reactive polymer; preferably the reactive polymer is a photoreactive polymer or copolymer. In other embodiments the immbolization material includes a binding pair.

In some embodiments the array includes multiple arrays, subarrays, or combinations thereof. An array having subarrays can be prepared by creating particular subsets of microparticles having unique self-encoding marker/probe pairs. In some embodiments the detection of the target is accomplished by determining a particular subset of microparticles according to its location on the array in combination with detection of the self-encoding marker/probe pairs.

The self encoding marker can include at least one detectable particle which can include fluorophores, quantum dots, radioisotopes, and magnetic particles. Combinations of these detectable particles can be used to provide a unique self-encoding marker.

The invention also includes methods of fabricating the arrays and the arrays themselves.

BRIEF DESCRIPTION OF THE DRAWINGS

FIG. 1 is a schematic diagram of an array and a method of preparing the array.

FIG. 2 is a schematic diagram of an array and a method of preparing the array.

FIG. 7 is a schematic diagram of subarrays and a method for preparing the subarrays.

DETAILED DESCRIPTION OF THE PREFERRED EMBODIMENTS

Figure 3:
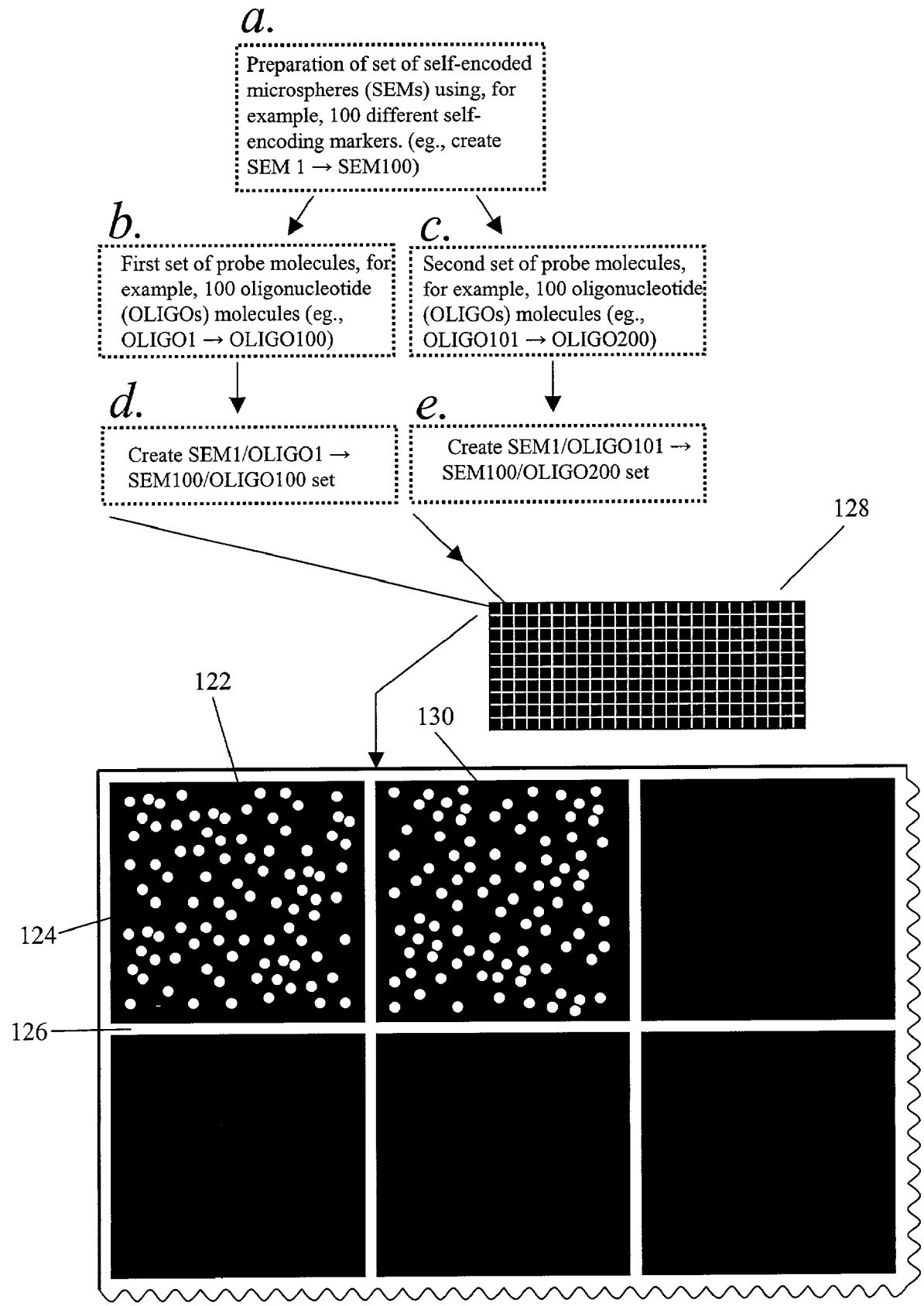
FIG. 3 is a schematic diagram of a method for preparing subsets of microparticles having self encoding marker/probe pairs and a method of preparing subarrays.

As used herein, "array" refers to a plurality of different probe molecules presented on a surface, where unique probe molecules are coupled to individual microparticles and the microparticles are randomly immobilized on a substrate. Each microparticle is also associated with a self-encoding marker thereby forming unique self-encoding marker/probe pairs, enabling detection of the individual microparticles and the identity of the probe. An array can present one set of microparticles having unique self-encoding marker/probe pairs or can present more than one set or more than one subset of microparticles having unique self-encoding marker/probe pairs thereby allowing multiple arrays, subarrays, or combinations thereof, on the substrate.

A "set" of microparticles having unique self-encoding marker/probe pairs generally refers to a plurality of microparticles having unique self-encoding marker/probe pairs wherein the plurality of microparticles presents all of the probe molecules to be arrayed on the substrate.

As used herein, "multiple array" refers to an array, that presents more than one set or subset of microparticles having unique self-encoding marker/probe pairs disposed at defined locations on the substrate.

As used herein, "subarray" refers to a portion of an array that contains a subset of microparticles which having a plurality of microparticles having unique self-encoding marker/probe pairs wherein the plurality of microparticles presents a portion of all the probe molecules arrayed on the substrate. An array typically includes more than one subarray, each subarray being different.

As used herein, "random" or "random distribution" or "randomly arrayed" refers to the arbitrary localization of an immobilized microparticle having a unique self-encoded marker/probe pair on a substrate by the method of the invention. For a particular set or subset of microparticles having unique self-encoded marker/probe pairs the localization of an individual microparticle having a unique self-encoded marker/probe pair within the set or subset is random on the portion of the substrate on which the set or subset is disposed. A particular microparticle having a having a unique self-encoded marker/probe pair can be randomly immobilized on the surface of a substrate even though the microparticles may be directed to patterned portions of the substrate. Therefore, microparticles can be ordered according to position on the substrate although the arrangement according to the unique self-encoded marker/probe pairs is random. Such embodiments are discussed herein. The location of a microparticle having a unique self-encoded marker/probe pair within the immobilized set or subset is not determined until a detection step is performed.

As used herein, a "probe" is a moiety that is immobilized on a substrate to form an array. Typically, according to the invention, the probe is coupled to a microparticle, and the microparticle is immobilized on a substrate, thereby forming a portion of an array. The probe is a molecule, a particle, or a cell that can specifically interact with a particular target. The probe can include naturally occurring or man-made molecules, and it can be used in its unaltered state or as aggregates with other species. Typically the specific interaction of the probe and the target is based on chemical bonds that establish affinity interactions between the probe and target, for example, between an antibody and an antigen, or specific interactions based on an arrangement of repetitive hydrogen bonding patterns, for example between an oligonucleotide and its complementary oligonucleotide. In one embodiment, the probe comprises a biological molecule, such as, for example, a nucleic acid. However, the probe can be any other molecule that specifically binds to a target. For example, the probe can be a protein, such as an immunoglobulin, a cell receptor, such as a lectin, or a fragment of any of these, for example, $F_{ab}$ fragment, $F_{ab'}$ fragments, and the like. In another embodiment, the probe can be a cell or particle, such as viral particle, and the target can be a molecule, cell, or other particle that can interact with the cell or particle.

As used herein, a "target" refers to one or more molecules, a particles, or a cells suspected to be present in a sample. For example, a target can be a nucleic acid. The target can specifically interact with a particular probe based on interactions exemplified above. The target can be detected and/or quantitated in the method or system of the invention. Typically the target is coupled to a "target marker" to allow detection of the target. The target can comprise naturally occurring or man-made molecules, and it can be detected in its unaltered state or as aggregates with other species. Examples of targets include antibodies, nucleic acids, receptors, hormones, drugs, metabolites, cofactors, peptides, enzymes, viral particles, cells and the like. In one embodiment, the target comprises a nucleic acid to be detected in a sample. The probe and target are typically members of a specific binding pair, wherein the members of the pair are known to bind to each other, while binding little or not at all to other nonspecific substances.

The term "sample" is used in its broadest sense. The term includes a specimen or culture suspected of containing target.

As used herein, the terms "complementary" or "complementarity," when used in reference to nucleic acids, specifically, a sequence of nucleotides such as a probe nucleic acid or a target nucleic acid, refer to paired sequences that are able form standard Watson Crick base-pairs. For example, for the sequence "5'-T-G-A-3'," the complementary sequence is "3'-A-C-T-5'." Complementarity can be "partial," in which only some of the bases of the nucleic acids are matched according to the base pairing rules. Alternatively, there can be "complete" or "total" complementarity between the nucleic acids. The degree of complementarity between the nucleic acid strands has effects on the efficiency and strength of hybridization between the nucleic acid strands.

The term "hybridization" is used in reference to the pairing of complementary nucleic acids. Hybridization and the strength of hybridization, specifically, the strength of the association between the nucleic acids, is influenced by such factors as the degree of complementarity between the paired nucleic acids, stringency of the conditions involved, the melting temperature ($T_m$) of the formed hybrid, and the G+C/A+T ratio within the nucleic acids.

As used herein, the term "nucleic acid" refers to any of the group of polynucleotide compounds having bases derived from purine and pyrimidine. The term "nucleic acid" can be used to refer to individual nucleotides or oligonucleotides, for example, a short chain nucleic acid sequence of at least two nucleotides covalently linked together, typically less than about 500 nucleotides in length, and more typically about 20 to 100 nucleotides in length. The term "nucleic acid" can also refer to long sequences of nucleic acid, such as those found in cDNAs or PCR products, for example, sequences that are hundreds or thousands of nucleotides in length. The exact size of the nucleic acid sequence according to the invention will depend upon many factors, which in turn depend upon the ultimate function or use of the nucleic acid.

Nucleic acids can be prepared using techniques presently available in the art, such as solid support nucleic acid synthesis, DNA replication, reverse transcription, and the like. Alternately, nucleic acids can be isolated from natural sources. The nucleic acid can be in any suitable form, for example, single stranded, double stranded, or as a nucleoprotein. A nucleic acid will generally contain phosphodiester bonds, although, in some cases, a nucleotide can have an analogous backbone, for example, a peptide nucleic acid (PNA). Nucleic acids include deoxyribonucleic acid (DNA), for example, complementary DNA (cDNA) ribonucleic acid (RNA), and peptide nucleic acid (PNA). The nucleic acid can include DNA, both genomic DNA and cDNA, RNA, or both DNA and RNA, wherein the nucleic acid contains any combination of deoxyribo- and ribo-nucleotides. Furthermore, the nucleic acid can include any combination of uracil, adenine, guanine, thymine, cytosine as well as other bases such as inosine, xanthenes, hypoxanthine and other non-standard or artificial bases. PNA is a DNA mimic in which the native sugar phosphate DNA backbone has been replaced by a polypeptide.

As used herein, "coupling" refers to the direct or indirect attachment of one moiety to another through the formation of at least one bond, which can include covalent, ionic, coordinative, hydrogen, or Van der Waals bonds, or non-chemical interactions, for example, hydrophobic interactions. For example, coupling of compound "A" to compound "D" can be direct and involve the formation of a covalent bond between "A" and "D", or coupling of compound "A" to compound "D" can be indirect and involve the presence of compound "B" and "C" where coordinative bonds exist between "A" and "B", and "C" and "D", and a covalent bond exists between "B" and "C". It is understood that according to this description that two moieties can be coupled to each other by numerous ways. Such coupling can include, but is not limited to, specific non-covalent affinity interations, for example streptavidin: or avidin:biotin interactions and hapten:antibody interactions; hydrophobic interactions; magnetic interactions; polar interactions, for example, "wetting" associations between two polar surfaces or between oligonucleotide/polyethylene glycol; formation of a covalent bond, for example, an amide bond, a disulfide bond, a thioether bond, an ether bond, a carbon-carbon bond; or via other crosslinking agents; or via an acid-labile linker. As used herein, "bonding" refers to the direct attachment of two moieties typically through a chemical bond.

"Hydrophilic" and "hydrophobic" are used herein to describe compositions broadly as water attracting and water repelling, respectively. Generally, hydrophilic compounds are relatively polar and often ionizable. Such compounds usually bind water molecules strongly. Hydrophobic compounds are usually relatively non-polar and non-ionizing. "Hydrophobic" refers to materials or surfaces that have a low affinity for water, are not readily mixed with or wetted by water, and which are generally water-repellant. Hydrophobic and hydrophilic are relative terms and are used herein in the sense that various compositions, liquids and surfaces can be hydrophobic or hydrophilic relative to one another.

The present invention provides a method for detecting target in a sample using arrays providing a plurality of microparticles having unique self-encoding marker/probe pairs. According to the invention, an array is provided that includes a set or subset of microparticles having unique self-encoding marker/probe pairs. Each self-encoding marker/probe pair includes a microparticle having a unique self-encoding marker that comprises at least one detectable species, and a probe, wherein the self-encoding marker is chosen to correspond with the probe. In one embodiment, sample suspected to contain a target is treated to couple a target marker to the target and then the sample containing target-marker labeled target is applied to the array, so that target marker-labeled target, if present in the sample, will hybridize with a probe associated with the array. In another embodiment, target marker is coupled to the target after binding of the target to the probe. Thereafter, bound target and target marker associated with the microparticle having the self-encoding marker/probe pair is detected using a detection scheme. The detection scheme involves detection of both the target marker and the self-encoding marker. Detection of the self-encoding marker allows for determination of the probe, and thus the identity of the bound target.

According to the invention, arrays are prepared by randomly disposing and immobilizing microparticles having unique self-encoding marker/probe pairs on the substrate wherein an immobilization material is used to immobilize the microparticles having unique self-encoding marker/probe pairs on the substrate. The location and identification of a microparticle bearing a particular self-encoding marker/probe pair is typically not determined until the detection step. In some embodiments the random disposing and immobilization of the microparticles having unique self-encoding marker/probe pairs can be performed on at least a portion of the substrate that has been patterned with the immobilization material. A patterned substrate can be used to form multiple arrays, subarrays, or combinations thereof. In one embodiment the microparticles are immobilized on the surface of the substrate via a polymer that has been disposed on the substrate. In another embodiment the microparticles are immobilized on the substrate by coupling the microparticles to the substrate surface via, for example, a binding pair or a crosslinking agent. The random disposing and immobilization of sets or subsets of microparticles having unique self-encoding marker/probe pairs can provide advantages relating to fabrication of arrays, since the precise location of a microparticle need not be predetermined. In addition the use of microparticles provides a greater surface area for probe coupling The invention contemplates methods for detecting target using the arrays of the invention, methods of making the arrays, and the arrays themselves. Also contemplated are kits for detecting target in a sample.

Arrays prepared according to the invention are fabricated on a solid support, also referred to herein as a "substrate". Preferably, the substrate comprises a integral support. Generally, the term "solid support" or "substrate" refers to a material that provides a two- or three-dimensional surface on which the microparticles of the invention can be immobilized. The composition of the solid support can be any sort of suitable material to which the microparticles can be directly or indirectly immobilized. Typically, the microparticles of the invention are coupled to the "substrate surface" via an immobilization material. The composition of the substrate can vary, depending upon the particular microparticles to be immobilized, as well as the desired surface characteristics in areas of the substrate that do not have microparticles immobilized on them, as will be discussed herein.

Preferably, the substrate does not interfere with the ability of the probe to bind target and is not subject to high amounts of non-specific binding. Suitable materials for the substrate include biological or nonbiological, organic or inorganic materials. Suitable solid substrates include, but are not limited to, those made of plastics, ceramic, resins, polysaccharides, silicon and silica-based materials, glass, metals, films, gels, membranes, nylon, natural fibers such as silk, wool and cotton and polymers. Suitable polymers include, but are not limited to, polystyrene, polyethylene, polyethylene tetraphthalate, polyvinyl acetate, polyvinyl chloride, polyacrylonitrile, polymethyl methacrylate (PMMA), butyl rubber, styrenebutadiene rubber, natural rubber, polypropylene, (poly)tetrafluoroethylene, (poly)vinylidenefluoride, polycarbonate, and polymethylpentene. In one embodiment, the substrate is prepared from a material that is suitable for use with a fluorescence detection device, for example, a fluorescence scanner or a fluorescence microscope. In this embodiment, the material for the substrate preferably does not interfere with the detection of the fluorescence signal associated with the array.

Preferably, the substrate comprises an integral surface for immobilization of the microparticles. The substrate can be either "substantially flat", meaning that the surface is substantially planar and has little or no surface configurations, or the substrate can have surface configurations such as raised portions, surface projections, etched areas, wells, and the like. The surface of the substrate preferably is provided by a single substrate.

The dimensions of the substrate can vary and can be determined by such factors, for example, as the dimensions of the array, and the amount of probe diversity desired. In some embodiments the substrate can provide a surface for a single array, an array containing multiple arrays, an array containing subarrays, or an array containing combinations of multiple arrays and subarrays. The arrangement of sets or subsets of randomly disposed microparticles on the substrate, which can be in the form of multiple arrays or subarrays, can be formed by pre-coating or coating the substrate with a compound or compounds that facilitate the immobilization of microparticles on the surface of the substrate, referred to as "immobilization material". As used herein, the term "pre-coating" or "coating" refers to the process of disposing a compound on a surface; the compound or compounds can be used for immobilizing the microparticle on the substrate. In some embodiments the substrate is precoated with a compound, for example, a polymeric compound, having photoreactive groups. Photoreactive groups can be used to couple various moieties of the invention to the substrate through the formation of chemical bonds. Examples of photoreactive groups are described below.

The microparticles of the invention can comprise any three-dimensional structure that can be immobilized on a substrate and coupled to the self-encoding marker and probe moieties. Typically the microparticles are spherular in shape. As used herein "spherular" refers to three dimensional shapes that include, spherical, spheroidal, rounded, globular shapes and the like. The size of the microparticle can be in the range of about 100 nm to about 100 µm in diameter. In preferred embodiments, the microparticles are of an appropriate size to be detected as individual particles using the imaging devices described herein. For example, if the resolution of the imaging device is 5 µm, it is preferable that the microparticles immobilized on the substrate be 10 µm or larger.

According to the invention, the microparticle can be fabricated from any suitable material. Suitable materials include, for example, polymers such as poly(methylmethacrylate), polystyrene, polyethylene, polypropylene, polyamide, polyester, polvinylidenedifluoride (PVDF), and the like; natural polymers such as cellulose, crosslinked agarose, dextran, and collagen; glass, including controlled pore glass (CPG) and silica (nonporous glass); metals such as gold, steel, silver, aluminum, copper, ferric oxide, and the like; magnetite, and the like. Examples of useful microparticles are described, for example, in the "Microparticle Detection Guide" from Bangs Laboratories, Fishers, Ind.

In some embodiments it is preferable that the microparticles are swellable, and become more porous when placed in an appropriate solution. As used herein, "swellable" refers to the ability of the microparticles to expand and become more porous when in an appropriate medium and can incorporate compounds or particles in a swollen state. Swellable microparticles are useful for impregnating a particle, for example, a detectable particle, which can be a portion of the self-encoding marker, into the microparticle. Such swellable microparticles are typically composed of polystyrene, or copolymers of polystyrene, and can be swollen in an organic solvent. Swellable microparticles can be useful for incorporating different types of detectable material, for example, a magnetic material. In other embodiments the microparticles can be impregnated with a combination of different types of detectable material.

Microparticles can also be obtained commercially from, for example, Bangs Laboratories (Fishers, Ind.), Polysciences (Germany), Molecular Probes (Eugene, Oreg.), Duke Scientific Corporation (Palo Alto, Calif.), Seradyn Particle Technology (Indianapolis, Ind.), and Dynal Biotech (Oslo, Norway). Commercially available microparticles can be modified further to provide the desired self-encoding marker and probe moieties on the microparticle.

The microparticles of the invention can possess one or more desirable properties, such as dimensional stability, optical properties, for example, size and color. The microparticles can also be chosen to provide additional desirable attributes, such as a satisfactory density, for example, a density greater than water or other solvent used in preparation of the array, or properties that allow the microparticle to be "self-encoded."

As used herein "detectable species" refers to a detectable moiety that can be associated with a microparticle. Typically, the self-encoding marker comprises at least one detectable species.

In one aspect, the microparticles of the invention can be described as "self-encoding." As used herein, the terms "self-encoding" or "self-encoded" refers to a unique detectable identity associated with the microparticle that allows one microparticle to be differentiated from another using the detection techniques described herein. The term "self-encoding marker" refers to one detectable species or a combination of detectable species, which serve to provide the microparticle with a unique identity that can be determined by one or more types of detection techniques. A self-encoding marker associated with the microparticle provides the self-encoded nature of the microparticles. According to the invention, a particular self-encoding marker serves as an identifier of a particular probe attached to the microparticle. Self-encoding of the microparticles allows the user to create unique marker/probe pairs, in which the self-encoding marker is associated with a particular probe.

Properties useful for self-encoding of the microparticles include, but are not limited to, fluorescence, size, shape, magnetic susceptibility, electrostatic properties, and the like. The self-encoded nature of each microparticle is typically associated with at least one type of detectable species, for example, a fluorescent compound, which is associated with the microparticle. In some embodiments the self-encoded nature is dependent on a combination of detectable species associated with a particular microparticle. For example, a first microparticle can be loaded with or coupled to a selected dye, such as a fluorescent dye that has an excitation/emission maxima of 350/440 nm. In this exemplary embodiment, the first microparticle associated with this fluorescent dye (350/440 nm) is also coupled to a probe nucleic acid sequence that is complementary to a nucleic acid for Gene A, wherein the nucleic acid for Gene A is suspected of being present in a sample. The microparticle associated with fluorescent dye (350/440) and the probe nucleic acid sequence for Gene A constitutes microparticle having a unique self-encoding marker/probe pair. A second microparticle can be loaded with or coupled to a different selected dye, such as a fluorescent dye that has an excitation/emission maxima of 488/520 nm. This second microparticle fluorescent dye (488/520 nm) associated is coupled to a probe nucleic acid sequence complementary to Gene B, wherein the nucleic acid for Gene B is suspected of being present in a sample. The microparticle including the fluorescent dye (488/520 nm) and the nucleic acid sequence that is complementary to a nucleic acid for Gene B constitutes a microparticle bearing a different unique self-encoding marker/probe pair. A plurality of microparticles bearing different self-encoding markers/probe pairs is generated and combined to form a "set" or "subset" of microparticles. The "set" or "subset" of microparticles is then disposed on a substrate or a portion of a substrate and on the substrate or a portion of the substrate the microparticles are randomly located. It will be apparent to one of skill in the art that any number of desired fluorescent dyes can be chosen to correspond to specific biomolecules, as desired.

Other useful markers that can be incorporated into or coupled to the microparticles include phosphors, quantum dots, radioisotopes, for example, molecules containing $^{32}P$, $^{33}P$, $^{35}S$, and fluorescence proteins, for example, the Green Fluorescence Protein.

A plurality of unique self-encoded microparticles can be created by, for each unique microparticle in the plurality, combining different self-encoding markers on the same microparticle. For example, microparticles having unique self-encoding marker/probe pairs can be created by incorporating or coupling the microparticle to two, or more than two, different fluorophores having different emission maxima. Preferably the emission maxima for the different fluorophores are distinct or are separable through use of band-pass filters, for example. Microparticles can also be prepared by incorporating or coupling the microparticle to two, or more than two different types of detectable species, for example, coupling the microparticle to a fluorophore and also to a radioisotope. By preparing microparticles having different combinations of detectable species, a vast number of microparticles with unique self-encoding markers can be prepared. This is especially useful when the array provides a substantial number of individually unique probes, thus requiring a substantial number of microparticles with individually unique self-encoding markers. In yet other embodiments, the microparticles provided in an array comprise a population of microparticles comprising a single fluorescent dye, as well as a population of microparticles comprising more than one fluorescent dye.

A plurality of unique self-encoded microparticles can also be created by, for each unique microparticle in the plurality, combining detectable species on the same microparticle at different concentrations. In addition to variation in the emission type, variation in the emission intensity, as a result of varying the concentration of the detectable species, can also provide additional variation to establishing a plurality of self-encoding markers. In one exemplary embodiment, 5 nmol of fluorescent dye A (488/520 nm) and 50 nmol of fluorescent dye B (350/440) are incorporated or coupled to microparticle C. Microparticle D has 50 nmol of fluorescent dye A (488/520 nm) and 5 nmol of fluorescent dye (350/440) incorporated or coupled to it. Although microparticle C and microparticle D include the same fluorescent dyes, they are detectable from one another because the intensity of emissions of fluorescent dyes A and B are different for microparticle C and microparticle D. Such fluorescent dyes and the intensity of emission of these dyes can be detected using imaging devices.

According to the invention, individual self-encoded microparticles can be distinguished in the array by taking the mean fluorescence intensity minus the background intensity at each emission wavelength for the selected dye or dyes. In the case of a microparticle encoded with multiple dyes, the mean fluorescence intensity minus the background intensity at each emission wavelength is taken and then divided by the fluorescence intensity of the alternate dye at its wavelength maxima to determine the signature of the particular dye ratio used to encode the microparticle. Unique sets of encoding dyes can be determined according to the formula (n!/p!) (n−p)!, where n is the number of dyes and p is the number of combinations (Michael et. al., (1998) Anal. Chem., 70:1242)

Examples of suitable fluorescent dyes include, but are not limited to, Indodicarbocyanine, Texas Red cadaverine, fluorescein, Oregon Green 488 (2',7'-difluorofluorescein), BODIPY-based dyes, that is dyes containing 4,4-difluoro-4-bora-3a,4a-diaza-s-indacene, Alexa 532, Cy 3, Cy5, tetramethylrhodamine, and other rhodamine derivatives. Microparticles can be coupled to or impregnated with the desired fluorescent dye or combination of fluorescent dyes to achieve the desired fluorescent properties that defines the self-encoding marker.

In another embodiment, the microparticles of the current invention can be self-encoded by embedding nanocrystals on or within the microparticles that confer particular optical properties to the microparticles. These nanocrystals can include quantum dots. For example, the self-encoding of microparticles can be achieved by embedding different sized quantum dots into microparticles at distinct ratios. These quantum dots can be composed of compounds such as zinc sulfide-capped cadmium selenide, indium aresenide, cadmium telluride, and the like. The optical properties of these quantum dots typically include a high luminescence and a size tunable emission and simultaneous excitation.

Different fluorescence emission from quantum dots is typically due to the size of the quantum dot itself. Fluorescence emission wavelength can be changed by altering the size of the quantum dot, and a single excitation wavelength can be used for the simultaneous excitation of different-sized quantum dots.

Quantum dots can be incorporated into and spatially separated from each other in the microparticles. Quantum dots that are sufficiently spaced from one another typically do not undergo fluorescence resonance energy transfer. Quantum dots can also be incorporated into microparticles at precisely controlled ratios, allowing one to generate a plurality of multicolor microparticles each with a different combination and amount of quantum dots.

Microparticles formed by emulsion polymerization of styrene, divinylbenzene, acrylic acid, and like materials are suitable for incorporating quantum dots. Preferably, microparticles composed of a material which allows the separation of incorporated quantum dots and does not allow the incorporation of larger particles and aggregates are preferred. In the preparation of microparticles including quantum dots, typically the largest size quantum, dots are loaded first and the smallest quantum dots are loaded last.

Microparticles containing quantum dots can also be sealed using a polymer material, for example a polysilane layer. A polymer material can stabilize the optical properties of the quantum dots, prevent exposure to reagents used when probing a sample, and also protect against temperature variations.

In one embodiment, the microparticles are self-encoded by incorporating a selected fluorescent dye into the microparticles. For example, the microparticles can be soaked in organic solvents containing a selected dye or dyes. The solvent swells the polymeric microparticles and allows the dyes to penetrate into the microparticles' cores. Excess solvent is then removed, for example, by vacuum filtration, entrapping the dyes in the interior regions of the microparticles. In one example, poly(methylsytrene)-divinyl benzene microparticles are rinsed in dimethylformamide. A solution containing the selected dye or dyes in dimethylformamide is then added to the microparticles, and the microparticles and solution are incubated with agitation for 24 hours. Excess dye is removed from the suspension by vacuum filtration using membrane filters, such as those provided by Millipore Company (Bedford, Mass.). The filtered microparticles are then sonicated and washed by centrifugation in distilled water containing 0.01% Tween 20 to remove residual dye on the outside of the microparticles.

Alternatively, fluorescent microparticles can be obtained commercially, for example, from Molecular Probes, Inc. (Eugene, Oreg.). Molecular Probes provides a variety of fluorescent microparticles under the product name Fluo-Spheres™, which are polystyrene microparticles loaded with various proprietary dyes with excitation and emission wavelengths ranging from near ultraviolet to the near infrared. These FluoSpheres™ can also be prepared with intensities lower than those of the regular selection, which can be desirable in some multicolor applications. Other commercial sources of fluorescent microparticles, for example, from Luminex Corporation (Austin, Tex.) can be used in accordance with the invention. Luminex provides a number of internally color-coded microparticles using a blend of different fluorescent intensities of two dyes. These microparticles can be provided with an activated surface, such as a carboxylated coating or avidin coating.

In some embodiments, self-encoding of the microparticle is accomplished by the size or shape of the microparticle. Differences in sizes can be visualized using equipment such as an image analyzer or an array scanner, for example. In order to differentiate microparticles according to size the difference between the sizes of microparticles is preferably not less than 50%, based on the diameter of the microparticles. For microparticles that are larger, for example approximately 50 µm, it is sufficient that the size difference is approximately 20%. Microparticles can also be distinguished according to shapes, for example, spherular or misshapen shapes. As used herein, misshapen microparticles display a shape that is discernable from a spherular shape and can be visualized using equipment such as, for example, an image analyzer, an array scanner, or a microscope. The shape of misshaped microparticles can be, for example, elongated or rod-like. In these embodiments, the self-encoding marker is a physical characteristic of the microparticle itself, such as the size or shape of the microparticle.

In some embodiments, self-encoding of the microparticle can be provided by magnetic or electrostatic properties of the microparticle. Magnetic microparticles are commercially available from, for example, Dynal Biotech (Oslo, Norway). Detection of electrostatic microparticles can be accomplished, for example, by placing the microparticle on a charged surface or in an electric field. One useful application is to place electrostatic microparticles on an array containing at least one electrode. A charge can be applied to the electrode, and depending on the charge associated with the microparticle, the microparticle will be attracted or repelled from the charge. Magnetic microparticles can be detected by placing them in a magnetized area. Magnetic properties of microparticles can be measured on assay surfaces adapted or use with readers for magnetic tapes, disks, and the like.

Visualization of the fluorescent dyes can be accomplished using any suitable visualization technique known in the art. Fluorescence imaging can be made using a modified epifluorescence microscope or a fluorescence confocal microscope. Suitable microscopes include, for example, an Olympus BX60 (Tokyo, Japan) or other similar microscopes. Fluorescence images from microscopy images can be analyzed for fluorescence intensity using computer software. Commercially available microscopy analysis software, for example, Image-Pro Plus (version 4.0) (Media Cybernetics, L. P., Silver Spring, Md.), can be used to define and count fluorescent signals automatically with optical detection systems. Alternatively, the method of fluorescence scanning can be used to visualize microparticles having self-encoded markers. Fluorescence scanners such as the Scan Array 5000 (GSI Lumonics, Billerica, Mass.) or Axon GenePix 4000A (Foster City, Calif.), which have resolution of approximately 5 µm, can be used for visualization.

It will be readily apparent to one of skill in the art, upon review of this disclosure, that an array can include a plurality of microparticles having combinations of the above-described detectable species. For example, a single array can utilize two or more specific types of detectable species, selected from fluorescent dyes, physical characteristics, such as size or shape, and magnetic or electrostatic properties. The choice of a particular combination of detectable species can be determined based upon the visualization techniques and equipment available to the user.

In some embodiments it is useful to generate a "set" of self-encoded microparticles. The members of a "set" of self-encoded microparticles are preferably readily distinguished from one another using the detection techniques as described herein. A set of self-encoded microparticles can contain approximately 2–10,000 different self-encoded microparticles but preferably contains approximately 50–200 different self-encoded microparticles. A set of different self-encoded microparticles can be used to form multiple arrays on a single substrate or subarrays on a single substrate by the methods discussed below. In some embodiments the set of microparticles can be coupled to "subsets" of probe molecules. The surface of the microparticles can, in some embodiments, be functionalized to provide "reactive groups" for coupling one or more probes to the microparticle, for coupling one or more detectable moieties to the microparticle, for coupling the microparticles to each other, or for coupling the microparticles to the immobilization material or the substrate. Suitable reactive groups can be chosen according to the nature of the moiety that is to be attached to the microparticle. Examples of suitable reactive groups include, but are not limited to, carboxylic acids, sulfonic acids, phosphoric acids, phosphonic acids, aldehyde groups, amine groups, thiol groups, thiol-reactive groups, expoxide groups, and the like. For example, carboxylate-functionalized microparticles can be used for covalent coupling of proteins and other amine-containing molecules using water-soluble carbodiimide reagents. Aldehyde-functionalized microparticles can be used to couple the microparticles to proteins and other amines under mild conditions. Amine-functionalized microparticles can be used to couple the microparticles to a variety of amine-reactive moieties, such as succinimidyl esters and isothiocyanates of haptens and drugs, or carboxylic acids of proteins. In another embodiment, sulfate-modified microparticles can be used when the user desires to passively absorb a protein such as bovine serum albumin (BSA), IgG, avidin, streptavidin, and the like. In another embodiment, the reactive groups can include such binding groups as biotin, avidin, streptavidin, protein A, and the like. Functionalized microparticles are also commercially available from a number of commercial sources, including Molecular Probes, Inc. (Eugene, Oreg.).

In some embodiments, microparticles can be coupled to other moieties through use of crosslinking agents. Commercially available crosslinking agents obtained from, for example, Pierce Chemical Company (Rockford, Ill.) can be used to link microparticles together via, for example, amine groups of the proteins. Useful crosslinking agents include homobifunctional and heterobifunctional crosslinkers. Two non-limiting examples of crosslinking agents that can be used on coated microparticles are di-succinimidyl suberate and 1,4-bis-maleimidobutane.

According to the invention, an array comprises a substrate and a plurality of microparticles associated with unique self-encoding marker/probe pairs immobilized on the substrate. As described herein, the probe comprises a moiety which can recognize a particular target, such as, for example, a nucleic acid with a unique sequence. In other embodiments the probe comprises a particle, a cell, or a portion of a cell. Given the teachings herein, one of skill in the art can select a desired probe, or set of desired probes, for fabrication of an array. Typically, the probe comprises a biological molecule.

In one embodiment the probe is a nucleic acid and the array includes a plurality of unique self-encoded microparticles coupled to a plurality of different nucleic acids defined by having different nucleic acid sequences. The nucleic acid probes coupled to the microparticles can be of any length but are preferably at least 6 nucleotides in length. More preferably the nucleic acid probes are between 8 and 200 nucleotides in length and most preferably the nucleic acids probes are between 12 and 50 nucleotides in length.

In another embodiment the probe can be a protein molecule, or a complex of protein molecules, and the array includes a plurality of microparticles having unique self-encoded markers, the microparticles also coupled to a plurality of different protein molecules, or a complex of protein molecules, each having an affinity for a target which can be present in a sample. The protein molecule can be, for example, an antibody that specifically recognizes a target or portion of a target, if present in a sample. The array can therefore comprise a plurality of self-encoded microparticles coupled to different antibody molecules, each with an affinity for a particular target, which may be present in a sample. Protein probes can include but are not limited to, for example, cell surface receptors, cell surface ligands, and intracellular proteins that interact specifically with another molecule.

In some embodiments a self-encoding microparticle "set" can be prepared, as described above, and individual members of the "set" can be coupled to unique probe molecules. In some embodiments, if the number of probe molecules greatly exceeds the number of individual self-encoding microparticles in the set, "subsets" of self-encoding marker/probe pairs can be generated. The following example provides a description of the preparation of subsets of microparticles having self-encoding marker/probe pairs. In an exemplary embodiment, a set of self-encoding microparticles is prepared which includes 100 unique self-encoding microparticle batches, and a set of probe molecules is prepared which includes 5000 unique probe nucleic acid molecules. The 5000 probe molecules are divided into 50 subsets of probes, each subset containing 100 probes. One subset of microparticles having self-encoding marker/probe pairs is prepared by individually coupling one member of the self-encoded microparticle set with one member of a probe subset. The set of self-encoded microparticles is used repeatedly to generate the 50 subsets of microparticles having self-encoding marker/probe pairs. In fabrication of an array, each of the 50 subsets containing microparticles having self-encoding marker/probe pairs can be disposed on the substrate at predetermined locations and are kept spatially separated. Detection of a microparticle having a particular self-encoded marker/probe pair is based on both the features of the detectable specie(s) on the microparticle and also the location of the subset on the substrate.

In some embodiments, it can be useful to group microparticles having self-encoding marker/probe pairs into subsets based on the common attribute of the probe molecule. For example, it may be useful to create subsets of microparticles having self-encoding marker/probe pairs based on tissue-specific or disease-specific expression of the target that binds expressly to the probe. Subsets can also be based on the type or class of molecule reactive within a probe, for example, transcriptional factors, such as repressors or activators, or cell surface factors, such as receptors.

As indicated, a microparticle with a unique self-encoding marker is coupled to a unique probe. Typically, an individual microparticle is coupled with a plurality of identical probe molecules. By providing multiple copies of the same probe molecule on a single microparticle, the sensitivity of the array can be increased. For example, following binding of the target to the probe, a higher signal to noise ratio can be achieved.

The number of probe molecules provided on each individual microparticle can be adjusted by the user to achieve the desired effect. The density of probe molecules, for example oligonucleotide or protein probe molecules, on a microparticle can be in the range of 1–260,000 probe molecules per 1 µm diameter microparticle. Typically, 40,000–50,000 probe molecules are immobilized per 1 µm diameter microparticle. Accordingly, the amount of probe molecules on the microparticle can also be dependent on the size of the microparticle used. However, depending on microparticle source and preparation, for example, the amount of streptavidin bound to a particular microparticle preparation, the amount of probe molecules coupled to the microparticles may vary. According to the method of the invention the density of probe molecules present on the array surface can be controlled with greater precision as compared to conventional methods of array preparation.

Probe molecules are typically coupled to the microparticles prior to deposition and attachment of the microparticles to the substrate. For example, the probe can be coupled to the microparticle in a suitable liquid media, such as phosphate buffered saline. Coupling of the probe to the microparticle prior to deposition of the microparticle can provide benefits in array preparation. For example, probes can be coupled to the microparticles at a higher density as compared to coupling of the probe to a conventional substrate with a flat surface. This can be accomplished using any of the coupling techniques discussed herein. Once the microparticles have been coupled with the desired amount and type of probe, these prepared microparticles can then be applied to the substrate and coupled thereto. Preferably, coupling of the microparticles prepared in this way does not interfere with the ability of the probe to bind with appropriate targets present in a sample. Coupling of probes to microparticles in solution is also generally more efficient than the coupling of probes to a conventional substrate with a flat surface, resulting in a low loss of probe during the coupling procedure. In addition, coupling of a probe to a microparticle in solution generally allows for more variability in the coupling process. In situations when the process of coupling of a probe requires particular conditions, for example the stirring of a probe in solution to allow coupling of the probe or proper presentation of the coupled probe, the use of microparticles, which can be mixed or agitated in solution, can allow these particular coupling conditions to be met.

According to the invention, probes can be coupled to the microparticles in any suitable manner. For example, the microparticles can be provided with reactive groups on the surface, as described above. Depending upon the reactive groups selected and the desired probe, the probe may or may not be modified prior to attachment to the microparticle.

Coupling of the probe to the microparticle can be accomplished by providing reactive groups on the microparticle, the probe, or both. Some reactive groups are discussed above for modification of the microparticles.

In some embodiments, the probe can be modified prior to coupling with the microparticle. For example, nucleic acids can be coupled to one member of a binding pair, and the microparticles coupled to the other member of the binding pair. Suitable binding pairs include but are not limited to avidin:biotin, streptavidin:biotin, and antibody:hapten. Examples of antibody hapten binding pairs include anti-digoxigenin Ab:digoxigenin or anti-trinitrophenyl Ab:trinitrophenyl. For example, a nucleic acid can be biotinylated, for example, using enzymatic incorporation of biotinylated nucleotides, or by cross-linking the biotin to the nucleic acid using methods known in the art. Biotinylated nucleic acid can then be coupled with streptavidin provided on the surface of the microparticles.

Nucleic acids can be modified in a variety of ways to afford coupling to the microparticles. For example, nucleic acid can be modified to provide a reactive moiety at the 3' or 5' end. Alternatively, nucleic acid can be synthesized with a modified base. In addition, modification of the sugar moiety of a nucleotide at positions other than the 3' and 5' position is possible through conventional methods. Also, nucleic acid bases can be modified, for example, by using N7- or N9-deazapurine nucleosides or by modification of C-5 of dT with a linker arm, for example, as described in F. Eckstein, ed., "Oligonucleotides and Analogues: A Practical Approach," IRL Press (1991). Alternatively, backbone-modified nucleic acids, such as phosphoramidate DNA, can be used so that a reactive group can be attached to the nitrogen center provided by the modified phosphate backbone.

Preferably, the modification of a probe, such as a nucleic acid, does not substantially impair the ability of the probe or nucleic acid to hybridize to its complement. In the case of nucleic acid, modification should preferably avoid substantially modifying the functionalities of the nucleic acid that are responsible for Watson-Crick base pairing.

In one embodiment, one or more photoreactive groups are randomly attached to the probe nucleic acid, for example along the backbone or at either their 3' or 5' ends. For example, the bases present on the nucleotides making up the nucleic acid possess numerous reactive groups that can be derivatized using a heterobifunctional photoreactive compound having both a photoreactive group and a thermochemically reactive group suitable for coupling to the bases. In this embodiment, thermochemically reactive groups, as described herein, can be used to couple the photoreactive group to the probe nucleic acid via reactive groups present on the nucleic acid. This approach typically results in a relatively nonselective derivatization of the nucleic acid, both in terms of the location along the backbone, as well as the number of photoreactive groups per nucleic acid molecule.

In an alternative embodiment, the oligonucleotide can be synthesized to incorporate chemically reactive groups at specific sites of the oligonucleotide, for example, along the backbone or at the 3' or 5' ends. For example, commercially available reagents or solid supports are available that permit the incorporation of amine groups at any of these locations in the oligonucleotide. These amine groups are then reacted with a photoreactive compound that includes a thermochemically reactive group, as described herein, resulting in formation of an amide bond between the photoreactive group and the oligonucleotide. Other electrophilic and nucleophilic species can provide similar coupling techniques.

In another embodiment, one or more of the nucleotide building blocks typically used in oligonucleotide synthesis can themselves be derivatized with a reagent containing a photoreactive group by attachment of the reagent to one of the reactive functionalities present on the base residue of the nucleotide. The resulting derivatized nucleotide reagent can be used in an automated synthesizer, under conventional reaction conditions, in order to incorporate the photoreactive group at designated points along the chain or at either end of the oligonucleotide. In addition, commercially available non-nucleotide reagents, used for incorporation of chemically reactive groups, can be reacted with the photoreactive compound to incorporate the photoreactive group, after which they can be used in the automated synthesizer to prepare the photoactivatable nucleic acids.

A variety of reagents are available for use in modifying nucleic acids. In another embodiment, photoderivatized nucleotides can be synthesized and incorporated into nucleic acids using enzymatic techniques. For example, a variety of reagents are available that can be used to label nucleic acids with biotin, fluorescein and digoxigenin (DIG). A nucleic acid can be labeled with a photoreactive dideoxyribonucleotide or deoxyribonucleotide, using a terminal transferase, in order to provide either single or multiple photoreactive groups at the 3' end of the nucleic acid. For example, a DIG-labeling kit called "DIG-High Prime" for use in random primed labeling of DNA with DIG-11-UTP is also available. "Biotin High Prime", Boehringer-Mannheim and "Fluorescein-High-Prime" products are also available. In a similar fashion, DNA can be random-primed with a photoreactive deoxyribonucleotide using the Klenow enzyme.

DNA Polymerase I enzyme can also be used to incorporate photoreactive groups into an oligonucleotide. By including photoreactive deoxyribonucleotides in the mixture of deoxynucleotide triphosphates (dNTPs), the resulting polymerized product will contain one or more photoreactive groups along its length. In addition, during polymerase chain reaction (PCR), a photoreactive deoxyribonucleotide can be included in the mixture of dNTPs for the labeling of amplification products. It is also possible to incorporate a photoribonucleotide into RNA, for example, by the use of an RNA polymerase such as SP6 or T7, and standard transcription protocols.

Alternatively, polypeptides, for example proteins, can be passively absorbed onto microparticles and then optionally crosslinked to the microparticles. Polypeptides are preferably absorbed onto the microparticles under conditions that promote the greatest interaction of hydrophobic portions of the polypeptide and the microparticle.

The array is generally fabricated by disposing a plurality of microparticles having unique self-encoding marker/probe pairs on a substrate and allowing the microparticles to become immobilized on the substrate. Immobilization of the microparticles can be accomplished by providing immobilization material which can couple the microparticles to the surface of the substrate.

As used herein, "immobilization material" collectively refers to compounds that are used to immobilize the microparticles to the surface of the substrate. In some embodiments the immobilization material can be a single compound, for example, a crosslinking agent or a polymeric material, which is in direct contact with both the surface of the substrate and the microparticle. In other embodiments the immobilization material can be at least two compounds, for example, two members of a binding pair. When two or more compounds are included in the immobilization material, these compounds can interact in series to link the microparticle to the surface of the substrate. In a preferred embodiment, a reactive immobilization material (RIM) is used for coupling the substrate to the microparticles. Reactive immobilization material can include chemically reactive groups, for example photoreactive groups, or thermally reactive groups. These reactive groups are typically responsive to an applied agent, such as light or heat. Activation of these groups can be used to link the treatable immobilization material to the substrate, microparticle, or other desired moieties.

In one embodiment, the substrate can be pre-coated with an organosilane material. Pre-coating with an organosilane material can be useful in providing a surface of the substrate that can form bonds with other immobilization material. In this embodiment, the substrate is cleaned, pretreated or cleaned and pretreated prior to attachment of the microparticles. The substrate (for example, a soda lime glass microscope slide) is silane treated by dipping it in a mixture of 1% p-tolydimethylchlorosilane (T-silane) and 1% N-decyldimethylchlorosilane (D-silane, United Chemical Technologies, Bristol, Pa.) in acetone, for 1 minute. After air drying, the slides are cured in an oven at 120° C. for one hour. The slides are then washed with acetone followed by dipping in distilled water. The slides are further dried in an oven for 5–10 minutes. Other pretreatment or washing steps will be apparent upon review of this disclosure. Optionally, portions of the substrate can be pre-treated with compounds to develop areas having different surface properties, for example, different regions of hydrophobicity or hydrophilicity.

In other embodiments, pretreatment of the substrate is not required, as will be apparent upon review of this disclosure. In these embodiments the substrate can be directly pre-coated with a compound, such as a polymeric compound.

In another embodiment the microparticles can be immobilized on a substrate by use of a polymer. In this embodiment the substrate is coated with a suitable polymer prior to or during the step of disposing the microparticles. Suitable polymers can be synthetic polymers which can include polyacrylamide, polymethacrylamide, polyvinylpyrrolidone, polyacrylic acid, polyethylene glycol, polyvinyl alcohol, and poly(HEMA), copolymers thereof, or any combination of polymers and copolymers. Natural polymers can also be used and include polysaccharides, for example, polydextrans, glycosaminoglycans, for example, hyaluronic acid, and polypeptides, for example, soluble proteins such as albumin and avidin, and combinations of these natural polymers. Combinations of natural and synthetic compounds can also be used. The polymers and copolymers as described can also be derivitized with a reactive group, for example a thermally reactive group or a photoreactive group.

In a preferred embodiment, the substrate is coated with a polymer or copolymer containing at least one photoreactive group, herein referred to as a 'photoreactive polymer'. Such photoreactive polymers can be prepared by the polymerization of monomers functionalized with photoreactive groups. Alternatively, the photoreactive polymer can be formed by the polymerization of monomers functionalized with photoreactive groups and other non-functionalized monomers, thereby forming photoactivatible copolymers.

According to this embodiment, photoreactive groups can be provided on a polymer. As used herein, a "photoreactive polymer" can include one or more "photoreactive groups." A "photoreactive group" includes one or more reactive moieties that respond to a specific applied external energy source, such as radiation, to undergo active species generation, for example, active species such as nitrenes, carbenes and excited ketone states, with resultant covalent bonding to an adjacent targeted chemical structure. Examples of such photoreactive groups are described in U.S. Pat. No. 5,002,582 (Guire et al., commonly owned by the assignee of the present invention), the disclosure of which is incorporated herein in its entirety. Photoreactive groups can be chosen to be responsive to various portions of the electromagnetic spectrum, typically ultraviolet, visible or infrared portions of the spectrum. "Irradiation" refers to the application of electromagnetic radiation to a surface.

Photoreactive aryl ketones are preferred photoreactive groups on the photoreactive polymer, and can be, for example, acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone and thioxanthone, and their ring substituted derivatives. Particularly preferred are thioxanthone, and its derivatives, having excitation wavelengths greater than about 360 nm.

The azides are also a suitable class of photoreactive groups on the photoreactive polymer and include arylazides ($C_6R_5N_3$) such as phenyl azide and particularly 4-fluoro-3-nitrophenyl azide, acyl azides (—CO—$N_3$) such as ethyl azidoformate, phenyl azidoformate, sulfonyl azides (—$SO_2$—$N_3$) such as benzensulfonyl azide, and phosphoryl azides $(RO)_2PON_3$ such as diphenyl phosphoryl azide and diethyl phosphoryl azide.

Diazo compounds constitute another suitable class of photoreactive groups on the photoreactive polymers and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as 3-trifluoromethyl-3-phenyldiazirine, and ketenes (—CH═C═O) such as ketene and diphenylketene.

Exemplary photoreactive groups are shown in Table 1.

TABLE 1

| Photoreactive Group | Bond Formed |
|---|---|
| aryl azides | Amine |
| acyl azides | Amide |
| Azidoformates | Carbamate |
| sulfonyl azides | Sulfonamide |
| phosphoryl azides | Phosphoramide |
| Diazoalkanes | new C—C bond |
| Diazoketones | new C—C bond and ketone |
| Diazoacetates | new C—C bond and ester |
| beta-keto-alpha-diazoacetates | new C—C bond and beta-ketoester |
| aliphatic azo | new C—C bond |
| Diazirines | new C—C bond |
| Ketenes | new C—C bond |
| photoactivated ketones | new C—C bond and alcohol |

The photoreactive polymer can, in some embodiments, comprise a photoreactive copolymer. The polymer or copolymer can have, for example, a polyacrylamide backbone or be a polyethylene oxide-based polymer or copolymer. Examples of a photoreactive polymers and copolymers include a copolymer of vinylpyrrolidone and N-[3-(4-Benzoylbenzamido)propyl] methacrylamide (BBA-APMA); another example is a copolymer of acrylamide and BBA-APMA. Other examples of photoreactive groups and their attachment to polymers can be found in this description. It is envisioned that a wide variety of photoreactive polymers and photoreactive copolymers can be synthesized according to the materials described herein which allow the immobilization of microparticles on the surface of the substrate.

The photoreactive groups of the photoreactive polymer can allow the formation of a covalent bond between the substrate and the photoreactive polymer thereby binding the polymer to the surface of the substrate. The photoreactive groups of the photoreactive polymer can also serve to crosslink to proximal polymeric strands together, allowing the formation of a network of covalently crosslinked polymeric strands that serve to immobilize microsparticles. In some embodiments, a nonphotoreactive crosslinking agent can be used to promote the formation of crosslinked polymeric strands. Use of a crosslinking reagent, for example bis-acrylamide, can depend on the location and number of photoreactive groups that are present on the polymeric strand.

In forming the polymeric matrix, the polymer can be applied to the substrate and then treated to crosslink the polymers. In one embodiment, a slurry including microparticles and polymer is disposed on the substrate and then the polymer is treated to crosslink the polymer, for example, by activation of reactive groups provided by the polymer.

Different concentrations of polymer can be present in the slurry but generally the concentration shouls be great enough to allow for immobilization of the microparticles. The concentration of the polymer can also depend on the size of the microparticles used. For example, the concentration of polymer is at least 0.625 mg/mL for a 1.0 μm microparticle in order to stably entrap the microparticle in the polymeric matrix.

In other embodiments the microparticles can be coupled to the surface of the substrate using members of a binding pair (for example, binding partner A and binding partner B). One member of the binding pair can be bound to a desired location on the substrate and the other member of the biding pair can be bound to the microparticle. The interaction between the binding pair member and the substrate or the microparticle can be accomplished by covalent, ionic, coordinative, or hydrogen bonding or combinations thereof. Non-limiting examples of partners (for example, Partner A and Partner B) in binding pairs are provided in Table 2:

TABLE 2

| Partner A of Binding Pair | Partner B of Binding Pair |
|---|---|
| antigen or hapten | anti-antigen or anti-hapten antibody or antibody fragment |
| Anti-antigen or anti-hapten antibody or antibody fragment | antigen or hapten |
| Hormone | hormone receptor |
| hormone receptor | Hormone |
| avidin, streptavidin, neutravidin, or avidin-containing compound or complex | Biotin or biotinylated compound or complex |
| biotin or biotinylated compound or complex | avidin, streptavidin, neutravidin, or avidin-containing compound or complex |

TABLE 2-continued

| Partner A of Binding Pair | Partner B of Binding Pair |
|---|---|
| protein A or G | Immunoglobulin |
| Immunoglobulin | protein A or G |
| Enzyme | enzyme cofactor or inhibitor |
| enzyme cofactor or inhibitor | Enzyme |
| lectin or organoborate | Carbohydrate |
| Carbohydrate | Lectin or organoborate |

Another method for coupling moieties of the invention is through a combination of chemical and affinity interactions, herein referred to as "chemi-affinity" interactions, as described by Chumura et al. (2001, Proc. Natl. Acad. Sci., 98:8480). Binding pairs can be engineered that have high binding specificity and a neglible dissociation constant by functionalizing each member of the binding pair, near the affinity binding sites of the pair, with groups that will react to form a covalent bond. For example, the substituents of each functionalized member can react, for example by Michael addition or nucleophilic substitution, to form a covalent bond, for example a thioether bond. Antigen:antiantigen antibody pairs, complementary nucleic acids, and carbohydrate:lectin pairs are example of binding pairs that can be functionalized to provide chemi-affinity binding pairs.

In other embodiments, the array can be fabricated by disposing, and optionally treating the immobilization material on the substrate so that sets or subsets of microparticles having unique self-encoding marker/probe pairs can be randomly disposed on the substrate.

In one embodiment, all or a portion of the surface of the substrate is coated with a reactive immobilization material and the reactive immobilization material is treated to bind it to the substrate. For example, a photoreactive polymer is coated onto the substrate and irradiated to form covalent bonds between the substrate and the photoreactive polymer. In another example, a member of a binding pair, for example biotin, is disposed on the surface of a substrate that has been modified to present chemical groups reactive towards the biotin and which binds biotin to the surface. Microparticles coupled to streptavidin can be immobilized on this biotin-coupled surface. Examples of members of binding pairs that can be used in this embodiment are shown in Table 2. In yet another example, a crosslinking agent can be coated on a substrate and used to couple the microparticle to the substrate. In some embodiments the concentration of the immobilization material can also be adjusted to provide a desired amount of immobilization material on the surface of the substrate. This, in turn, can be useful for providing an array surface where the amount of bound immobilization material controls the spacing of the microparticles. In these embodiments, the microparticles can be disposed on a substrate that has been coated with the immobilization material and the microparticles become immobilized randomly on the substrate via the immobilization material.

In other embodiments, a pattern of immobilization material can be formed on the substrate allowing microparticles to be coupled to the substrate at locations where immobilization material is present. Forming of a pattern of immobilization material on a substrate can be useful for creating a substrate that contains multiple arrays or subarrays of microparticles. The pattern of immobilization material formed on the substrate can be of any shape or size. As shown in FIG. 1, the immobilization material can be patterned on the substrate in multiple squares on the surface of the substrate, thereby forming "patches" of immobilization material 110. The microparticles become immobilized on or within the patches when the microparticles are disposed on the substrate.

The pattern can be formed on the surface by a variety of methods. In one embodiment, as illustrated in FIG. 1, a substrate 102 can be coated with an immobilization material (IM) having photoreactive groups thereby forming photoreactive IM-coated substrate 104. A mask 106 is placed over the photoreactive IM-coated substrate 104 and then exposed to an light source to activate the photoreactive groups and bind the immobilization material to areas on the substrate 102 surface that are not protected by the mask 106. Unbound photoreactive IM can be removed by, for example, a washing step, resulting in a patterned substrate 108 containing patches 110 of bound immobilization material. In this embodiment, a preferred photoreactive immobilization material is a photoreactive polymer, for example, a copolymer of vinylpyrrolidone and N-[3-(4-Benzoylbenzamido) propyl]methacrylamide (BBA-APMA); or a copolymer of acrylamide and BBA-APMA.

In another embodiment as illustrated in FIG. 2, a mask 106 is placed over a substrate 102 which is then sprayed with an immobilization material (IM) reactive with the surface of the substrate 104. The mask 106 can be removed leaving a pattern of immobilization material resulting in a patterned substrate 118 containing patches 120 of bound immobilization material.

In some cases, the patterned substrate 118 can be treated if the immobilization material contains reactive groups.

Patterned substrates can be used for the fabrication of arrays containing subarrays or multiple arrays. In one embodiment, as illustrated in FIG. 3, the fabrication of an array having subarrays is demonstrated. FIG. 3a depicts the preparation of a self-encoded microparticle set by coupling different combinations of detectable species to microparticles. The self-encoded microparticle set of 3a contains 100 different self-encoding microparticles; however the set can contain any number of different self-encoding microparticles as defined by the number of different self-encoding combinations. FIGS. 3b and 3c depict two different "subsets" of probes. Each subset typically contains a different group of probes, however redundancy in probe presence between subsets can occur. In this example, self-encoded microparticles from FIG. 3a are coupled to probes from FIG. 3b to create a subset of microparticles having unique self-encoding marker/probe pairs as shown in FIG. 3d. Another subset of unique self-encoded marker/probe pairs is created by coupling the microparticle set of FIG. 3a with the probe subset of FIG. 3c. Any number of subsets of microparticles with self-encoding marker/probe combinations can be prepared. Typically, the number of subsets is defined by the number of unique probe molecules to be displayed on the array.

Upon preparation of subset(s) of microparticles having self-encoding marker/probe pairs, the members of the set can be mixed together for disposing on a patterned substrate 128. Disposing of the subsets of microparticles can be performed by any acceptable method, for example, by pin printing or by application with a needle.

In this example, the patterned substrate 128 having patches of immobilization material, can be fabricated by any of the methods described herein. A preferred method is to prepare a substrate with a pattern of photoreactive polymer. Subsets of mixed microparticles having self-encoding marker/probe pairs can be individually deposited on separate patches of the patterned substrate 128. Microparticles from the first subset, FIG. 3d, are disposed within a first patch 124 on the substrate thereby forming a subarray on a patch 124 wherein the microparticles of the subset are randomly distributed. An example of a randomly distributed microparticle 122 is illustrated. Microparticles from the second subset, FIG. 3e, can be deposited on a separate second patch 130. The patches are typically separated by a border 126 of uncoated substrate. The width of this border 126 is preferably at least as great as the diameter of an individual microparticle 122, more preferably at least twice the diameter of the microparticle.

The process of depositing subsets of microparticles having unique self-encoding marker/probe pairs can be repeated or performed simultaneously to provide the substrate with a desired number of subarrays. The location of a deposited subset or a pattern is typically noted to provide the user with information regarding the probe identity during the detection step.

In some embodiments subsets of microparticles having self-encoding marker/probe pairs can be deposited more than once on a substrate thereby creating an array with multiple subarrays.

Figure 4:
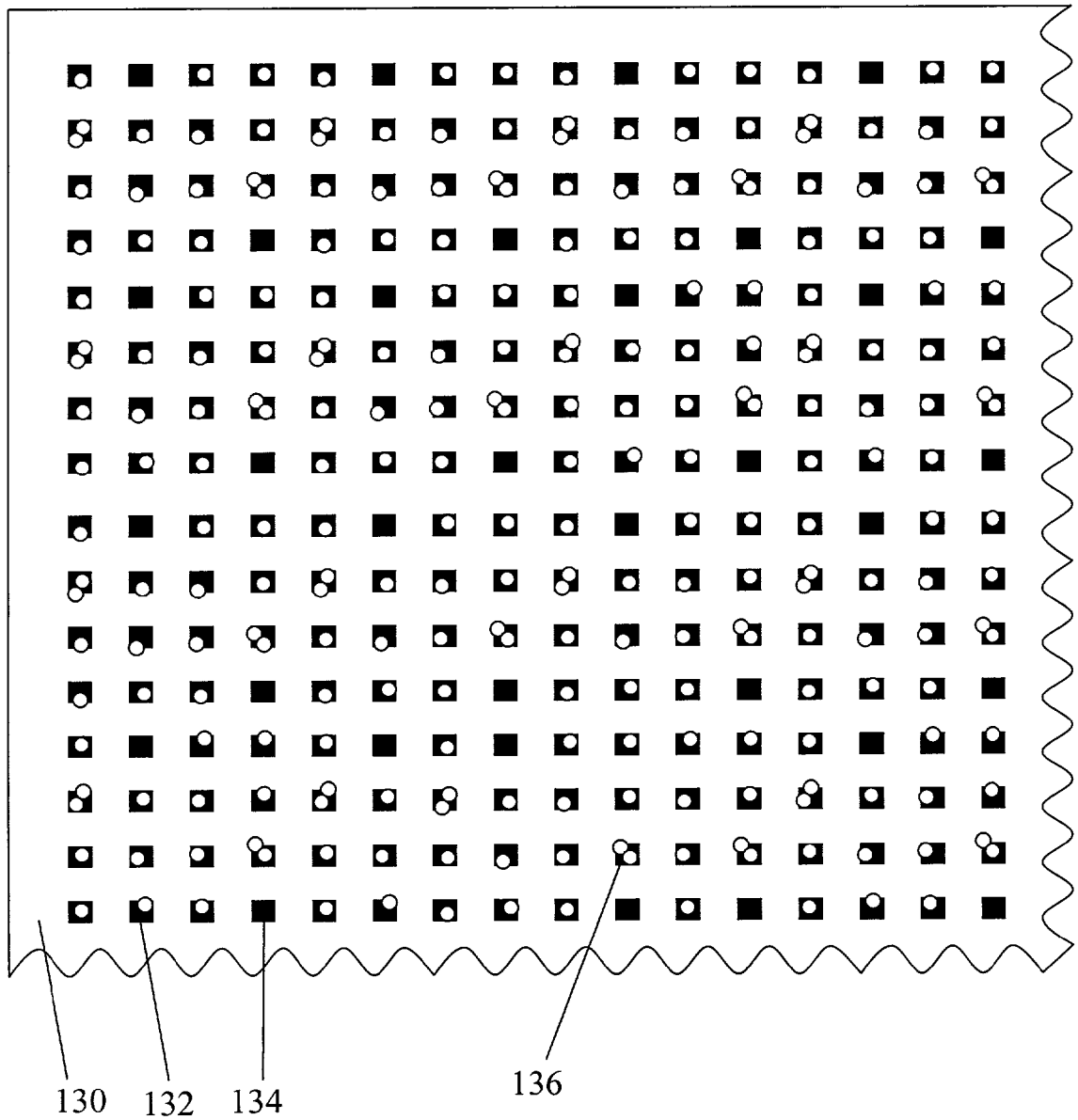
FIG. 4 is a schematic diagram of an array and a method of preparing the array.

In another embodiment as illustrated in FIG. 4, immobilization material can be patterned on the substrate 130 to provide a plurality of patches that are sized to accommodate a desired number of microparticles, for example, one microparticle per patch. Upon the disposing of a set of microparticles having self-encoded marker/probe pairs individual microparticles can be spatially separated on the substrate. Preferably, the majority of the microparticles on the substrate are individually separated wherein single microparticle patches 132 are displayed. However, it is possible that microparticle-devoid patches 134, double microparticle patches 136, or patches containing more than two microparticles are displayed.

Figure 5:
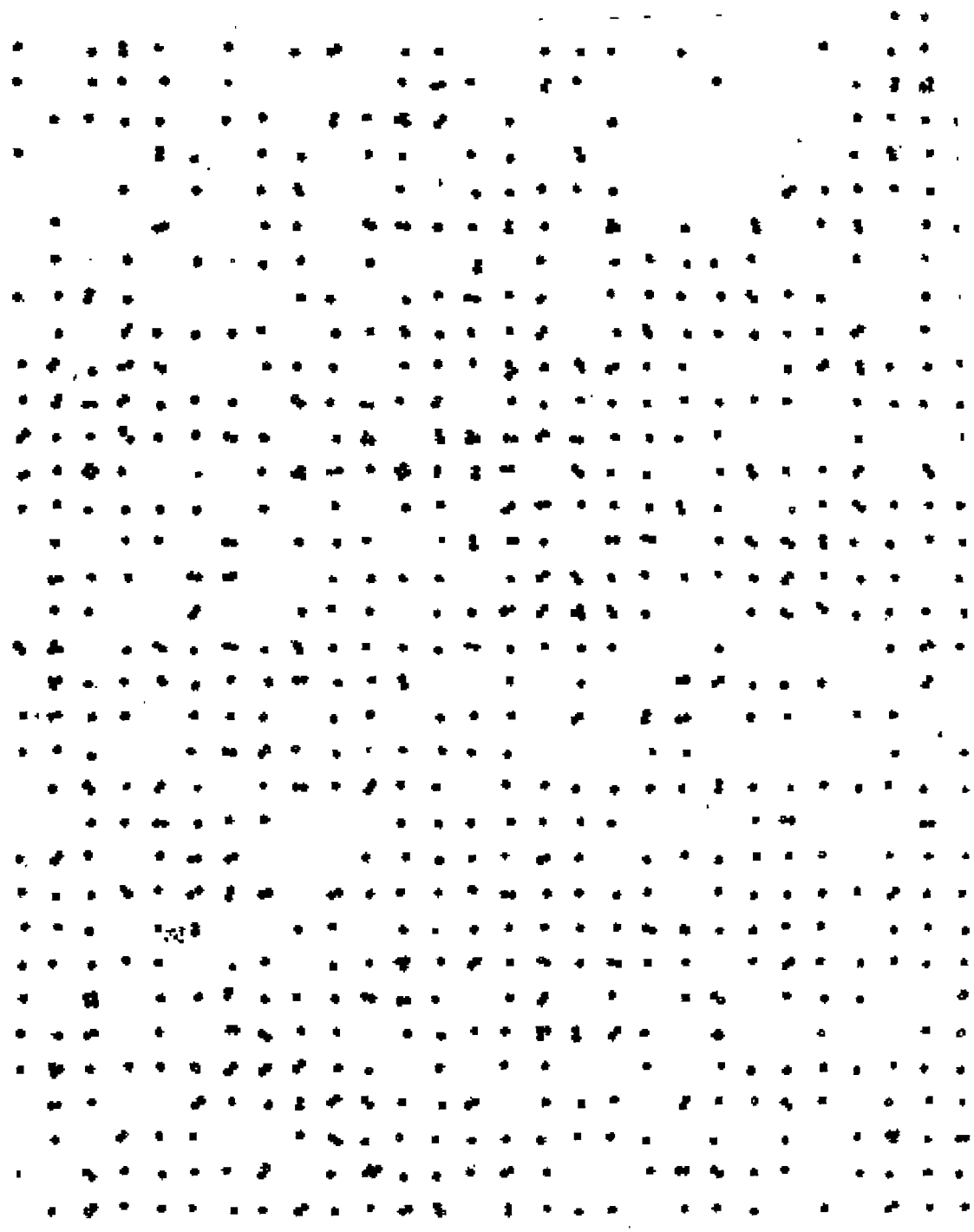
FIG. 5 is a photomicrograph of a portion of an array containing microparticles.
Figure 6:
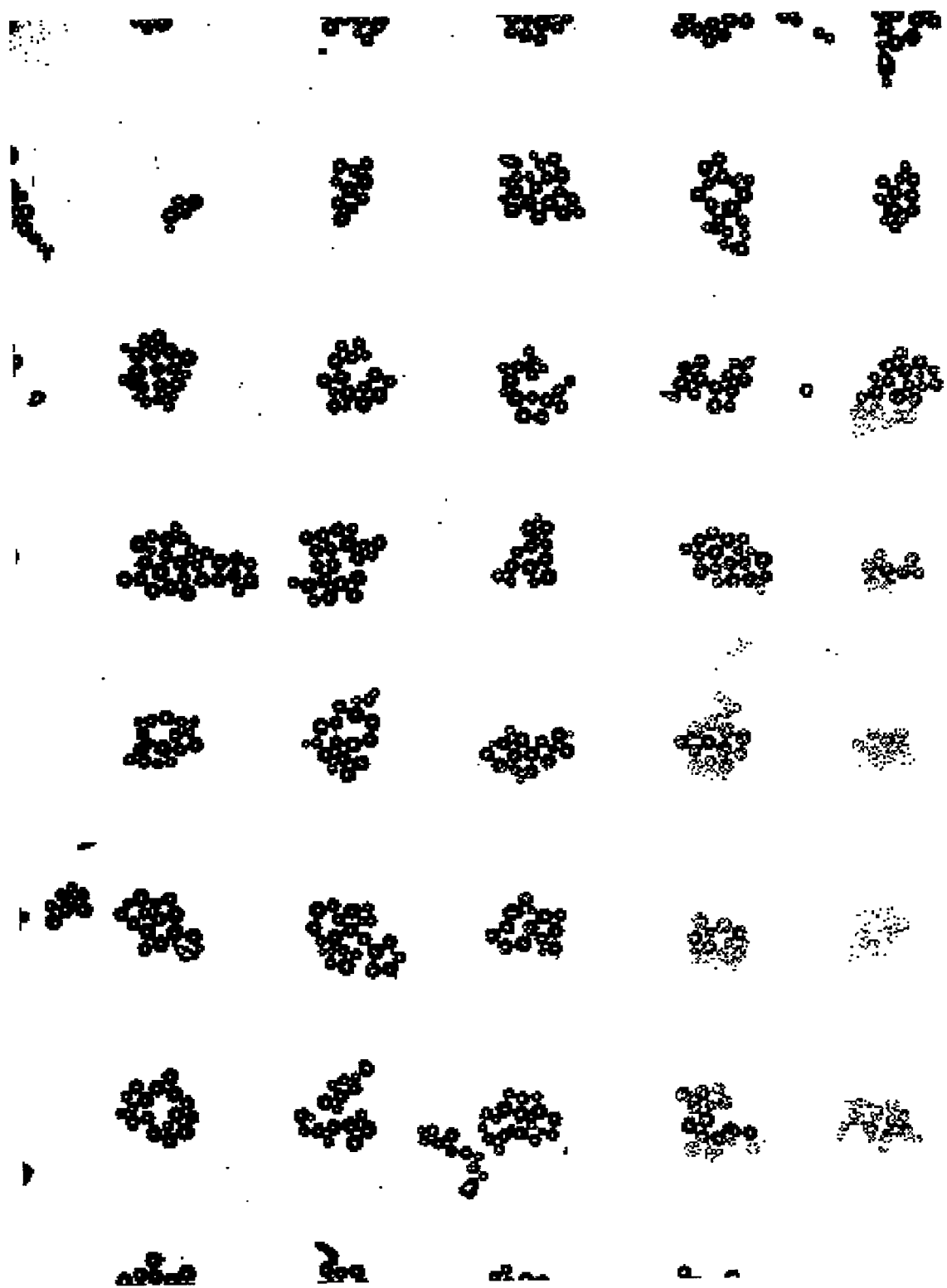
FIG. 6 is a photomicrograph of a portion of an array containing microparticles.

FIG. 5 shows a photomicrograph of a substrate having microparticles separated on the surface of a patterned substrate. The substrate was patterned to create patches that were sized to accommodate approximately one microparticle per patch. FIG. 6 shows a photomicrograph of a substrate having microparticles separated on the surface of a patterned substrate. The substrate was patterned to create patches that were sized to accommodate multiple microparticles per patch.

In another embodiment, as shown in FIG. 7, immobilization material can be patterned on the substrate to provide a plurality of patches which are grouped at predetermined locations on the substrate. For example, as shown in FIG. 7a, one group of patches is located in coordinate ($X_a$, $Y_a$) on the substrate. Typically, these groups are separated by a border of uncoated substrate where microparticles will not be immobilized preferably wider than the width of at least two patches. As shown in FIG. 7b a set or subset of microparticles having self-encoding marker/probe pairs is deposited on the group of patches. In this example the patches are sized to accommodate approximately one microparticle per patch and the number of patches within the group is greater than or equal to the number of unique microparticles having self-encoding marker/probe pairs of the set or subset, therefore allowing the entire set or subset to be represented in one group of patches.

For example, the pattern can be printed on the surface using, for example, a printing pin or a jet printer. In a preferred method, the pattern is generated by using a mask having a negative image of the pattern that is to be generated on the surface of the substrate. Use of a mask for generating a pattern is particularly useful for fabrication of arrays wherein the matrix-forming polymer contains photoactivatable groups and the activated groups are able to form bonds with the substrate and couple the polymer to the surface of the substrate In yet another embodiment, a plurality of microparticles are coupled to the substrate prior to application of microparticles intended to bear probe molecules. According to this embodiment, a plurality of "unloaded" microparticles are deposited onto and coupled to the substrate prior to application of microparticles that are to be coupled to one or more probe molecules. This application of unloaded microparticles provides an intermediate layer between the substrate and microparticles that will bear probe molecules. According to this embodiment, this intermediate layer can provide increased surface area for attachment of the marker/probe pairs, thereby increasing the loading density of the array. The coating of unloaded microparticles can cover some or the entire substrate surface. Additionally, "unloaded" microparticles can be used to provide reasonable spacing to distinguish signals from the self-encoding marker and target marker on separate microparticles.

In some embodiments, it can be desirable to alter the spacing of microparticles having self-encoding marker/probe pairs immobilized on the substrate. This can be accomplished in any desirable manner, for example, by providing microparticles that do not contain probe molecules. Preferably, the amount of space between the microparticles can be adjusted by altering the ratio of the amount of polymer to the amount of microparticles to the amount of solvent during deposition of the microparticles. An increase in the space between the microparticles can be achieved by increasing the amount polymer or decreasing the amount of microparticles, or a combination of the two.

In other embodiments, spacing of microparticles containing probe molecules can be altered by providing "unloaded" microparticles; that is, microparticles that are not coupled to any probe molecules. These unloaded microparticles can be provided in a suitable ratio to the number of microparticles that are coupled to probe molecules, to achieve the desired spacing. According to the current invention, the ratio of microparticles containing probe molecule to unloaded microparticles can be in the range of 1:1 to 1:20.

In some embodiments of the invention, it can be desirable to provide multiple copies of a specific microparticle having a unique self-encoding marker/probe pair on a single array. This "redundancy" of the microparticle having a unique self-encoding marker/probe pair on the array can provide increased sensitivity of the resulting array, since a probe will be located at more than one location on the array. As a result of this redundancy, a particular target will be capable of binding to at least one portion of the array. For example, in one embodiment, the array can contain a particular microparticle having a unique self-encoding marker/probe pair that is immobilized on the substrate at 1 to 10 different locations. In this embodiment, detection of the target associated with the redundant microparticles having a unique self-encoding marker/probe pair will take place at a number of different locations on the array.

In one embodiment, the sample suspected to contain a target is treated to label the target. As used herein, "target marker", refers to the detectable moiety that is coupled or bound to the target and used to determine the presence of the target, which can be present in a sample. As contemplated in this invention, a target marker comprises a moiety that is detectable using standard techniques known in the art. Examples of suitable labels include, but are not limited to, fluorophores, phosphors, and radioisotopes.

When the target to be detected comprises RNA, the RNA target can be labeled using molecular biology techniques, such as in vitro run-off transcription to generate a labeled RNA sample using RNA polymerases, for example T7, T3, or SP6 RNA polymerases. Kits for labeling RNA are available from various sources, for example, Ambion, Inc. (Austin, Tex.). This technique can be particularly useful in generating labeled RNA from, for example, a cDNA library that has been cloned into a vector with the appropriate promoters for RNA polymerase transcription. Techniques can also be used to generate labeled DNA, for example, nick translation, PCR amplification, random priming, or primer extension. These techniques can be useful for generating labeled DNA from for example, cDNA libraries or genomic DNA libraries. Modified DNA nucleotides for use as labels can also be created from Reverse Transcriptase reactions. For example, an RNA sample, such as a polyA-RNA sample can be used as a template in a reaction containing Reverse Transcriptase, polyT oligonucleotide primer, and modified nucleotide to generate labeled-cDNA. Techniques for labeling DNA can be found in various technical references, for example, Current Protocols in Molecular Biology (Ausubel et al., ed., 1990, Greene Pub. Associates and Wiley-Interscience: John Wiley, New York).

RNA and DNA targets can be labeled using modified nucleotides, for example fluorophore-coupled nucleotides, such as Fluorescein-5[6]-carboxyamidocaproyl-[5-(3-aminoallyl)uridine 5'triphosphate (Sigma, St. Louis, Mo.), biotin-coupled nucleotides, such as ($N^6$ [N-(Biotyinyl-ε-aminocaproyl)-6-aminohexylcarbamoylmethyl]adenosine 5'-triphosphate) or other modified nucleotides, for example, 5-(3-aminoallyl)uridine 5'-triphosphate (Sigma, St. Louis, Mo.) in order to enable detection of the DNA or RNA. Secondary fluorophore-coupled reagents, for example, Streptavidin-Cy3 (Caltag, Burlingame, Calif.) can be used to for indirect detection of the modified nucleic acid. Radioactive nucleotides, for example $^{32}$P-, $^{33}$P-, and $^{35}$S-labeled ribonucleotides and deoxyribonucleotides can be incorporated into the target DNA or RNA present in a sample. These modified nucleotides can also be used to label sample nucleic acids in other ways, for example, by 5' or 3' end-labeling with enzymes such as polynucleotide kinase or terminal transferase. Optionally, kits and instructions for coupling modified nucleotides to nucleic acid samples can be obtained commercially from, for example, CALBIOCHEM (San Diego, Calif.). Labeled target can optionally be purified by methods such as gel filtration or purification, spin columns, or selective precipitation.

In another embodiment, the sample is a protein sample suspected to contain a protein target. The protein sample can be obtained from a tissue sample, such as a biopsy, or from a fluid sample containing cells, for example blood or bone marrow, or from other body fluids, for example, plasma, sweat, saliva, or urine. A protein sample can be recovered from body fluid by a variety of techniques, for example by precipitation, filtration, or dialysis. A protein sample from cells, for tissue or body fluid, can be prepared by the lysis or solubilization of cells in detergents, optionally using methods such as sonication or homogenization. Ionic or non-ionic detergents can be used, for example, sodium dodecyl sulphate (SDS), Triton X-100, sodium deoxycholate or CHAPS. Cells can also be disrupted in the presence of chaotropic reagents, such as urea or guanidine salts. Other reagents can be added to the detergent or chaotropic reagent, such as a buffer, for example Tris or HEPES, and salts, for example KCl or NaCl. Other compounds can be utilized which stabilize the protein sample, for example, protease inhibitors, such as PMSF, pepstatin, or EDTA. However, a variety of methods and buffer compositions are available for the lysis or disruption of cells for protein extraction and are commonly known in the art. This information can be found in various references, for example, Current Protocols in Protein Science (Coligan et al., eds., 1996, John Wiley & Sons, New York, N.Y.).

The protein sample is preferably labeled in such a way to enable detection of the protein target and to retain the ability of the protein target to interact with the probe coupled to the microparticle. Reagents are available that allow the coupling of a fluorophore to an amino acid residue on a protein target. Amine-reactive groups, for example, succinimidyl esters, including sulfosuccinimidyl esters, isothiocyanates and sulfonyl chlorides, or dichlorotriazines, aryl halides and acyl azides are available as fluorophore probes and can be used for protein target labeling. A variety of these amine-reactive fluorophore probes are commercially available, for example, Alexa Fluor® 350 carboxylic acid, succinimidyl ester; 4,4-difluoro-5-(2-thienyl)-4-bora-3a,4a-diaza-s-indacene-3-propionic acid, succinimidyl ester (BODIPY® 558/568, SE); and 6-carboxy-4',5'-dichloro-2', 7'-dimethoxyfluorescein, succinimidyl ester (6-JOE, SE) (Molecular Probes, Eugene, Oreg.). In other circumstances it can be desirable to label the protein target with a fluorescent thiol-reactive derivative, for example, N,N'-didansyl-L-cystine (Molecular Probes, Eugene, Oreg.). Alternatively other reagents, for example fluorescent dyes containing a hydrazine group, an aromatic diazonium salt, or an amine group can be used to label the protein sample.

The protein target can also be coupled to a fluorescent protein, for example the Green Fluorescent Protein (GFP), using commercially available bifunctional crosslinking reagents, for example NHS-ASA (Pierce Chemical, Rockford, Ill.). Other bifunctional crosslinking agents that are reactive toward amine, sulfhydryl, carbohydrate, carboxyl and hydroxyl groups are commercially available (for example, Pierce Chemical, Rockford, Ill.) and can be used for coupling a protein of interest to the protein target. The protein target can also be coupled to a primary reagent for secondary fluorophore detection. In some embodiments, the protein can be modified by, for example, sulfo-NHS-biotin, and then coupled to a secondary fluorophore reagent, for example Streptavidin-Cy3.

Other methods of labeling a protein sample for detection are available. Such methods include, for example, protein iodination using $^{125}I$ and protein phosphorylation using $^{32}P$ or $^{33}P$ and a protein kinase can be used.

The target can also be a particle, for example, a viral particle, a portion of a cell, a cell, or a subpopulation of cells. These targets can display molecules on their surfaces that allow them to bind a particular probe that can be present in the array. The binding of the probe and the molecule present on a viral particle, a portion of a cell, a cell, or a subpopulation of cells can be useful in identifying and quantifying the target which can be present in a sample. For example, the array can be useful in determining the presence and quantity of different sub types of lymphocytes present in a sample. The viral particle, cell, or a portion of a cell can be labeled for detection by a variety of means, for example, by labeling with an antibody that is coupled to a fluorophore. The labeled antibody can be chosen to react specifically with a target, which can be a viral particle, a portion of a cell, a cell, or a subpopulation of cells. Alternatively, the target can be labeled by incorporation of a fluorescent dye into a portion of the target, for example, the membrane. Such dyes, for example, PKH-67 GL (Sigma, St. Louis, Mo.) or a fluorescent lipophilic probe, CM-DiI (Molecular Probes, Eugene, Oreg.), are commercially available and can be used to label cells or other targets.

It is understood by one of skill in the art that there are a wide variety of techniques available for protein labeling and that the technique chosen can depend on the protein or proteins available in the sample targeted for labeling.

Given the description herein, one of skill in the art can select the desired labeling scheme depending upon the target to be detected. While nucleic acids and proteins have been described with particularity, it will be clear that the teaching herein can be applied to label samples suspected to contain other types of targets, including, but not limited to, small molecules and the like.

Once formed, the array of the invention can be used to detect target suspected to be contained in a sample. In use, a sample is modified to provide labeled target, as described herein. The modified sample is then applied to the array, and the array and sample are maintained under conditions suitable to allow specific binding, for example, the hybridization of complementary nucleotides, between the probe and target, if present. Such specific binding conditions can be determined using techniques known in the art, depending upon the target to be detected.

After binding, excess sample can be removed, for example, by washing, and the remaining hybridized targets can be interrogated. The arrays of the invention can be used to detect any desired target suspected to be present in a sample. Interrogation of a sample can involve one or more visualization steps depending on the types of markers used for the target detection and microparticle detection. The label and detection marker can be chosen to allow detection of each using the same instrumentation, for example, a CCD camera or suitable fluorescence reader, although this is not required.

Typically, visualization of the results of an assay using the array of the invention involves one or more steps. Visualization of an analytical signal from the target marker, and visualization of the microparticle identity via the self-encoding marker to determine the identity of probe molecule associated with the microparticle can be accomplished in one step or more than one step. Visualization of the markers is dependent on the type of markers used.

In one embodiment, both the target marker, associated with target, and self-encoding marker, associated with a particular microparticle, are visualized using fluorescence microscopy. In this embodiment, presence of the target marker can be determined using a first wavelength associated with the fluorescent particle chosen for the target marker. The location and identity of a particular microparticle can be determined by switching to a second wavelength that is associated with the fluorescent particle chosen for the self-encoding marker coupled to or incorporated into the microparticle. Preferably, only those microparticles giving rise to an analytical signal need to be detected and decoded according to the invention.

The commercial fluorescent scanners described above have the capability to scan four different wavelengths, potentially allowing one to detect at least two self-encoding wavelengths and one target fluorescence wavelength. Commercially available self-encoded microparticles, such as those manufactured by Luminex, are designed to work with 532 nm target excitation, one of the common wavelengths of commercial scanners. One commercial scanner system, the Packard BioSciences ScanArray 5000 (Billerica, Mass.) has four wavelengths available for excitation (488 nm, 543 nm, 594 nm, and 633 nm). To create a simple self-encoding microparticle system it would be necessary to use labeled target at one wavelength, preferably 488 nm because many common oligonucleotide dyes exist for this wavelength (Fluorescein and its mimics) and because it would be less likely to overlap with the self-encoding dyes. At least two other wavelengths would then be used for the self-encoding dyes. One example would be to label the microparticles with a Texas Red dye (T-6134, Molecular Probes, Eugene, Oreg., excitation 596/emission 620 nm) which has little or no overlap with fluorescein, and a longer wavelength dye such as BODIPY 630/650 (D-10000, Molecular Probes, Eugene, Oreg., excitation 630/emission 650 nm). Based on its fluorescence absorbance and emission spectra, BODIPY 630/650 should adsorb a small fraction of the 596 nm light exciting the Texas Red dye, but none of the 488 nm target wavelength. To determine the corresponding spectral profile, the fluorescence at 594 and 633 nm excitation of each batch of self-encoded microparticles with a given ratio of Texas Red/BODIPY dyes would be ascertained prior to the assembly of the microarray and the overlap accounted for. This system could potentially be extended to include dyes at the 543 nm wavelength as well, because there is little light adsorbed by fluorescein derivatives at that wavelength. Given at least two and potentially three different dyes at different ratios, the number of uniquely self-encoded microparticles is large, at least 1000 (10 different ratios of each dye).

Visualization techniques can include, for example, spectrometric techniques such as UV/VIS, IR, fluorescence, chemiluminescence, mass spectrometry, or other methods known in the art, or combinations thereof.

It will be apparent to those skilled in the art that changes may be made to embodiments as described herein without deviating from the scope of the claimed invention. The following examples are provided to illustrate, but are not intended to limit, the present invention.

EXAMPLES

Example 1

Polypropylene and silanated glass slides (1×3 in.×1 mm) were used in the preparation of substrates in array fabrication. Glass microscope slides were obtained from Erie Scientific, Portsmith, N.H. (catalog # 2950-W). These soda lime glass microscope slides were silane treated by dipping in a mixture of 1% v/v p-tolyldimethylchlorosilane (T-Silane) and 1% v/v n-decyldimethylchlorosilane (D-Silane, United Chemical Technologies, Bristol, Pa.), each in acetone, for 1 minute. After air drying, the slides were cured in an oven at 120° C. for one hour. The slides were then washed with acetone followed by dipping in deionized water. The slides were further dried in an oven for 5–10 minutes. Polypropylene slides were obtained from Cadillac Plastics (Minneapolis, Minn.).

The silanated glass or polypropylene slides were then washed in acetone or isopropanol. The washed slides were then dip-coated in a 1 mg/ml solution of photo-Polystyrene (pPS) in toluene. pPS was prepared by pulverizing 3.05 g Polystyrene MW 500 (Polysciences Inc., Warrington, Pa.) with mortar and pestle and then dissolving the pulverized polystyrene in approximately 50 mL of carbon disulfide (Aldrich, Milwaukee, Wis.). A reaction flask was flushed with argon gas to ensure an anhydrous atmosphere and the dissolved polystyrene was placed in the flask. 2.91 g aluminum chloride (Aldrich, Milwaukee, Wis.) was added to the dissolved polystyrene, followed by the dropwise addition of then 2.5 mL of benzoyl chloride (Aldrich, Milwaukee, Wis.). The reaction mixture was then stirred at room temperature under Argon for 30 minutes, followed by refluxing the mixture for twelve hours. The mixture was then cooled and the solvent decanted off the reacted polymer. The polymer was triturated in methanol until a yellow solid was formed. This solid was washed with methanol and then dissolved in choloroform and precipitated from solution by methanol addition. This process yielded 1.16 g of yellow solid. Alternatively, the slides can be dip-coated in benzoylpolystyrene (Cat. #7917 Lancaster Synthesis, Windham, N.H.). The coated slides were air dried and irradiated for two (2) minutes with broad spectrum ultraviolet light (320–390 nm) using a Dymax LightWelder PC-2 (Dymax Engineering Adhesives, Torrington, Conn.) having a typical power output of 2 mW/cm$^2$. The lamp was positioned approximately 10 cm from the slides. Following irradiation, the slides were rinsed with toluene to remove unbound pPS. The pPS-coated slides were then immersed in an aqueous solution of 5 mg/mL biotinylated triblock (Dow Polyglycol B40-2500) for five (5) minutes, followed by irradiation for two (2) minutes and rinsing in isopropanol. The pPS-coated surface bound the biotinylated triblock surfactant effectively, creating a surface with uniformly distributed biotin moieties as determined by streptavidin-coated microparticle binding. Uniform distribution of biotin moieties was also determined by binding of fluorescently labeled avidin solution and determining the fluorescence pattern on the slides.

Magnetic, polystyrene-encapsulated microparticles, coupled to a flurorescent blue dye (excitation/emission maxima of 490/515 nm) and streptavidin were obtained from Bangs Laboratories (Product # CM01F; Fishers, Ind.). The streptavidin concentration was measured by biotin-conjugate binding and was determined to be 9.86 µg biotin-alkaline phosphatase/mg microbeads and 0.77 µg biotin-FITC/mg microbeads per manufacturer's measurement. The microparticles had a diameter of 0.96 µm and a density of 1.7 g/cm$^3$ (1.305e+12 microparticles/g). The prepared microparticles were washed once in phosphate buffered saline, pH 4.6 (PBS) including 0.1% bovine serum albumin (BSA) and 0.1% Tween 20 (PBS-B-T). After washing, the microparticles were resuspended in PBS-B-T. The biotinylated slide, prepared as described above, was soaked with PBS-B-T for thirty (30) minutes at room temperature. The phosphate buffer was then gently rinsed away with deionized water and centrifuged dry.

The washed microparticles were then added to the biotinylated slide at a concentration of 1 mg/mL (approximately 1.305 e+9 microparticles/ml) The microparticles and slide were incubated at room temperature for 20 to 30 minutes with gentle mixing by hand, with a three-dimentional motion, every few minutes.

Example 2

An array was formed by immobilizing microparticles on the substrate in the presence of a crosslinking agent, where the microparticles affinity bound the substrate and were coupled together by the presence of a crosslinking agent. pPS-coated slides, as prepared in Example 1, and streptavidin- and fluorophore-coated microparticles, as described in Example 1, were used in this example.

Amine-reactive N-hydroxysuccinimide (NHS) ester cross-linking reagent, disuccinimidyl suberate (DSS; Cat.#21555; Pierce Chemical, Rockford, Ill.) stock solution was prepared by dissolving DSS in dimethylformamide (DMF) at a concentration of 10 mg/mL. DSS stock solution was then diluted in PBS to a concentrations of 0.05, 0.025, 0.25, and 0.38 mg/mL DSS.

The PBS/DSS solution was then added to the washed microparticle suspension (as described in Example 1) and the microparticles had a concentration of 1 mg/ml in the final solution. The final concentration of DMF was kept below 5%, to avoid potential solvent damage to polystyrene microparticles and streptavidin.

The PBS/DSS/microparticle mixture was added as a slurry to the biotinylated slide. The PBS/DSS/microparticles mixture and biotinylated slide were incubated at room temperature for 20 to 30 minutes with gentle mixing by hand, with a three-dimentional motion, every few minutes. This step allowed the DSS to crosslink covalently attached streptavidin molecules on different microparticles, thereby forming microphere-microparticle linkages. DSS also crosslinked streptavidin molecules on the same microparticle using available primary amines of the streptavidin molecules. Streptavidin molecules on the microparticles also affinity bound the biotin on the slide surface and the DSS crosslinking did not reduce this affinity binding.

After incubation of the microparticles and slide, the slide is gently washed with a 0.1% Tween 20 solution, followed by rinsing with deionized water. The slide is then centrifuged dry in a slide rack holder in a clinical centrifuge (rotor radius=8 cm) at a speed in the range of 500–1000 RPM. The prepared substrate was stored until use under ambient conditions.

Example 3

An array was formed by immobilizing microparticles on the substrate by first providing a monolayer of microparticles on the substrate and then providing a subsequent layer of microparticles that became crosslinked in the presence of a crosslinking agent. pPS-coated slides, as prepared in Example 1, and streptavidin- and fluorophore-coated microparticles, as described in Example 1, were used in this example. The DSS crosslinking agent, as prepared in Example 2, was used in this example.

Microparticles coated with streptavidin were applied to the substrate and incubated to allow the streptavidin to non-covalently affinity bind to the biotin provided on the substrate. This coating provides a monolayer of streptavidin-coated microparticles. The coated substrate was washed to remove unbound microparticles. Thereafter, a solution containing microparticles was applied as a slurry to the substrate containing a monolayer of streptavidin coated microparticles.

The substrate and slurry were incubated at room temperature for 20 to 30 minutes with gentle mixing by hand, with a three-dimentional motion, every few minutes. After incubation of the microparticles and slide, the slide is gently washed with a 0.1% Tween 20 solution, followed by rinsing with deionized water. The slide is then centrifuged dry in a slide rack holder in a clinical centrifuge (rotor radius=8 cm) at a speed in the range of 500–1000 RPM. The prepared substrate was stored until use under ambient conditions room temperature.

Example 4

As shown in this example, an array was fabricated without pretreatment of the substrate surface. Microparticles were prepared by coupling a probe to the microparticle, followed by preparation of a slurry containing a photoreactive polymer and the probe-coupled microparticles. These prepared microparticles were then applied to a substrate to form an array.

Magnetic, streptavidin-coated fluorescent microparticles (0.96 µm) were obtained from Bangs Labs, (Fishers, Ind.) as described in Examples 1–3. The microparticles, were washed twice with deionized water and resuspended in 25 mM phosphate buffered saline, pH 8, at 10 mg/mL.

The streptavidin-coated microparticles were coupled to oligonucleotide BN30. BN30 is a 30-mer with a 5' biotin modification and a 3' amine (Integrated DNA Technologies, Coralville, Iowa). Coupling was performed using 5 nmole/ml of BN30 and 1 mg/ml of microparticles (five-fold excess of biotinylated oligonucleotide, based upon the supplier's stated biotin binding capacity) in 25 mM PBS, pH 8. The coated microparticles and oligonucleotide were incubated for 30 minutes at room temperature with gentle agitation. After incubation, the microparticles were washed with deionized water and resuspended at 20 mg/ml in deionized water.

A slurry of 37 mg/ml photoreactive poly(vinylpyrrolidone) (PV01; SurModics, Inc., Eden Prairie, Minn.) in water was combined with the microparticle solution at a ratio of 9:1(10×dilution of microparticle solution in PV01). The slurry was printed onto an acrylic surface (obtained from Cadillac Plastics, Minneapolis, Minn.) using a Microgrid II arrayer (Biorobotics, Inc. Cambridge, UK) with an average spot size of 100 µm and a center to center spacing of 250 µm, providing approximately 16 spots/mm$^2$. The printed substrate was irradiated for two (2) minutes as described in Example 1 with the addition of a beneath a cut-off filter (315 nm) to avoid potential nucleic acid damage, while gelling the PV01 solution. After irradiation, the substrate was rinsed with 1×PBS, 0.1% Tween 20.

The arrays prepared by the above method were stable to washing and touching, while samples that were not irradiated were not stable. Fluorescence scanning and light microscopy were used to determine the presence and location of the microparticles Sample containing nucleic acid complementary to probes of the array prepared as described above were interrogated as follows. Sample containing target nucleic acid was applied to the array and incubated. As described in Example 5.

Target was detected on the array with a ScanArray 5000 fluorescence scanner (Packard Bioscience, Billerica, Mass.).

Example 5

An array was fabricated by applying a suspension of microparticles to a substrate having a surface patterned with a polymer. Hydrophilic microparticles, which can be coupled to oligonucleotides or other biomolecules, were captured in the polymer when in aqueous solution and remain trapped there upon drying. A polymer pattern was formed approximately of the same size order as the bead diameter. Microparticles in the size range of 100 nm to 50 µm can be used for formation of an array, however, a preferred range is about 1 to 50 µm. Separate polymer spots were formed and there was approximately one microparticle per polymer spot.

Using this method a DNA microarray can be created using self-encoded microparticles wherein every unique self-encoded microparticle is coupled to a unique oligonucleotide sequence. Mixing various self-encoded oligonucleotide-coupled microparticles in the suspension would result in a random array of single microparticles, each microparticle/spot containing a different oligonucleotide sequence that can be probed.

An aqueous solution of 10 mg/ml photoreactive poly(vinylpyrrolidone) (PV01; SurModics, Inc., Eden Prairie, Minn.) was coated onto a hydrophobic glass slide as detailed in Example 1. Alternatively, the PV01 solution can be allowed to dry down in air on the slide. The coated slide was then irradiated for two minutes with ultraviolet light as detailed in Example 5 (Dymax Lightwelder) through a patterned mask (fabricated at the University of Minnesota, Minneapolis, Minn.), with structural features on the order of 1–100 μm. The mask used has four arrays of different sized patterns (200 μm spots, 500 μm center to center spacing, 100 μm spots, 250 μm center to center spacing, 50 μm spots, 100 μm center to center spacing, and 10 μm spots, 50 μm center to center spacing) and any pattern can be used for preparation of the array. Each of the four arrays measures 7.4×7.4 mm².

Irradiation served both to crosslink the PV01 to itself and to covalently bond it to the surface of the slide. After irradiation, the slide was washed with deionized water and isopropanol to remove excess PV01 from the non-irradiated areas of the pattern.

A suspension of 1.0 mg/ml streptavidin-coated silica microparticles (Cat no. SS06N, Bangs Laboratories, Fishers, Ind.) was placed over the patterned area of the slide created above in a 0.5M NaCl aqueous solution. The microparticles were allowed to settle for 15 minutes, after which a brief washing step with water was performed to remove microparticles which had not entered the polymeric matrix. At this point the microparticles were imaged by visible microscopy as shown in FIG. 5 to ensure that single microparticles formed in the array.

When utilizing oligonucleotide-coupled microparticles immobilized in the polymer pattern, the array can be washed with deionized water and then 1×PBS with 0.5% Tween-20. The array can then be incubated at 45° C. for 2 hours in 4×SSC and then subjected to a final deionized water wash. The thoroughly washed arrays can then be subjected to a standard protocol for hybridization of a target nucleic acid.

A typical hybridization can include, for example, 2.5 μL of a 33 fM solution of a fluorophore-coupled target nucleic acid in hybridization buffer (5×SSC, 0.1% SDS, 0.1 mg/ml salmon sperm DNA) per cm² (array area) placed between a coverslip and the array surface. The slides can then be placed in hybridization chambers and heated in a water bath at 45° C. for 2 hours. The coverslips can then be removed with a stream of 4×SSC buffer and the slides can then be washed with 2×SSC/0.1% SDS for five minutes at 45° C., followed by a 0.2×SSC wash for one minute at room temperature, and finally a wash of 0.1×SSC for one minute at room temperature. The slides could then be spun dry and the target oligonucleotide detected by methods described below.

Fluorescent target oligonucleotides can be detected on the microarray with either a commercial fluorescence microscope (Olympus BX 60, Tokyo, Japan) or a commercial fluorescence scanner using confocal fluorescence microscopy (Packard BioSciences, ScanArray 5000, Billerica, Mass.). The microparticles used in fabrication of the arrays can be chosen according to the resolution capabilities of the detection equipment. Currently, a standard fluorescence microscope can detect a microparticle in the size range of 1–50 μm diameter. Fluorescence scanners currently possess not greater than 5 μm resolution. A 5 μm area is illuminated in the focal plane of the slide and represents one pixel. Single microparticles would be detectable if the diameter is approximately 10 μm.

Example 6

Different matrix-forming materials were used to immobilize microparticles on a substrate illustrating the use of various reactive polymers for the fabrication of arrays. First, different polymers were disposed and treated on a substrate to provide immobilization material on the surface of the substrate. This was followed by disposing the microparticles on the substrates which were immobilized via the treated polymers. Four different photoreactive polymers were used to immobilize 9.9 μm diameter silica microparticles on substrates. These photoreactive polymers PA04, PA05, PV01, and PV05 are all commercially available from SurModics, Inc. (Eden Prairie, Minn.). PA04 and PA05 are copolymers of acrylamide (AA) and N-[3-(4-Benzoylbenzamido)propyl] methacrylamide (BBA-APMA) with differing ratios of BBA-APMA:AA. Similarly PV01 and PV05 are copolymers of vinylpyrrolidone (VP) and N-[3-(4-Benzoylbenzamido)propyl] methacrylamide (BBA-APMA) with differing rations of BBA-APMA:VP. Additionally a control material, PR03 (ethylene(4-benzoylbenzyldimethylammonium)dibromide; SurModics, Inc. Eden Prairie, Minn.; described in U.S. Pat. No. 5,714,360 to Swan et al., issued Feb. 3, 1998, commonly owned by the assignee of the present invention, the disclosure of which is incorporated herein in its entirety), a non-polymeric photoreactive compound, was evaluated.

Each photoreactive compound was dissolved in deionized water at a concentration of 2.5 mg/ml. Each solution was printed with 25 gauge disposable needles (PrecisionGlide Needles, Becton Dickinson and Co., Franklin Lakes, N.J.) and an x-y programmable stage (CAMM-3, Roland Digital Group, Irvine, Calif.) onto glass microscope slides which had been functionalized with silanes, as in Example 1, and onto acrylic slides (Cadillac Plastics, Minneapolis, Minn.). This printing forms a pattern of approximately 300–400 μm diameter spots on the substrates.

The patterned slides were irradiated for two minutes with ultraviolet light as detailed in Example 1. After irradiation, 500 μl of an aqueous solution of 2 mg/ml 9.9 μm diameter silica microparticles (SS06N, Bangs Laboratories, Fisher, Ind.) was placed over the patterned area for one minute to allow the microparticles to become immobilized by the polymer matrices. The slides were then rinsed with 0.1% v/v Tween-20 aqueous solution to remove any free microparticles.

Following this, the substrate was washed to remove loosely bound microspheres. The substrate was washed three times with 1×PBS (pH 7.4) with 0.1% v/v Tween-20, and then rinsed with deionized water. At this point, each was imaged with a fluorescence microscope (Olympus BX 60, Tokyo, Japan), to determine microsphere loss in the various photoreactive polymer matrices. After imaging, the substrates were incubated in a solution of DB02 wash buffer (Surmodics Inc. Eden Prairie, Minn.) for 1 hour at 50° C., followed by two rinses with deionized water. The substrates were then incubated in a solution of 4×SSC/0.1% SDS for two hours at 50° C. and rinsed in deionized water. This was the final step at which imaging was done to evaluate the respective polymers. Results are summarized in Table 3.

TABLE 3

| Photo-reactive Compound | Sub-strate | Presence of microparticles before washes | Presence of microparticles after PBS-Tween wash | Presence of microparticles after high salt wash (4X SSC) |
|---|---|---|---|---|
| PA04 | Glass | Present | Some loss | Significant loss |
| PA04 | Acrylic | Present | Some loss | No loss |
| PA05 | Glass | Present | Some loss | No loss |
| PA05 | Acrylic | Present | No loss | Some loss * |
| PV01 | Glass | Present | No loss | No loss |
| PV01 | Acrylic | Present | No loss | No loss |
| PV05 | Glass | Present | No loss | No loss |
| PV05 | Acrylic | Present | No loss | No loss |
| PR03 - non-polymer control | Glass | Present | Some loss | Complete loss |
| PR03 - non-polymer control | Acrylic | Present | Some loss | Complete loss |

\* Sample was touching another slide during the wash.

We claim:

1. A method for detecting a target in a sample, the method comprising steps of
    a) providing an array comprising
        (i) a substrate; and
        (ii) a plurality of microparticles randomly immobilized on the substrate via an immobilization material, wherein each microparticle comprises a self encoding marker and a probe coupled to the microparticle, wherein each self-encoding marker and probe comprises a unique self-encoding marker/probe pair, and wherein the probe is configured and arranged to specifically bind the target;
    b) applying the sample suspected of containing the target coupled to a target marker to the array;
    c) maintaining the sample and array under conditions to allow binding of the target to the probe; and
    d) detecting the self-encoding marker coupled to the microparticle, and detecting the target marker associated with the microparticle
    wherein the immobilization material comprises a reactive polymer, the reactive polymer bound to the substrate, and the microparticles immobilized on the substrate via the reactive polymer; and
    wherein the reactive polymer comprises a photoreactive polymer having at least one photoreactive group and the photoreactive group is selected from the group consisting of aryl ketones, arylazides, acyl azides, sulfonyl azides, phosphoryl azides, diazoalkanes, diazoketones, diazoacetates, and ketenes.

2. The method of claim 1 wherein the reactive polymer comprises polymers selected from the group consisting of functionalized polyacrylamide, polymethacrylamide, polyvinylpyrrolidone, polyacrylic acid, polyethylene glycol, polyvinyl alcohol, poly(HEMA), copolymers thereof, and combinations thereof.

3. The method of claim 1 wherein the immobilization material is patterned on the substrate to form patches of immobilization material and the microparticles are immobilized on the patches of immobilization material.

4. The method of claim 3 wherein the plurality comprises more than one subset of microparticles having unique self-encoding marked probe pairs and the subsets of microparticles are individually disposed on separate patches of immobilization material on the substrate.

5. The method of claim 4 wherein the step of detecting further comprises determining the location of the subset, thereby, in combination with the detection of the self-encoding marker, at least allowing determination of the identity of the probe.

6. The method of claim 1 wherein the microparticles are functionalized with a reactive compound and the reactive compound is used to couple the microparticles to the immobilization material, the self-encoding marker, the probe, or any combination of the above.

7. The method of claim 6 wherein the reactive compound includes reactive groups selected from the group consisting of carboxylic acids, sulfonic acids, phosphoric acids, phosphonic acids, aldehyde groups, amine groups, thiol groups, thiol-reactive groups, and expoxide groups.

8. The method of claim 1 wherein the probe is an antibody probe and the target is a molecule present in the sample that is specifically recognized by the antibody.

9. The method of claim 1 wherein the self-encoding marker comprises at least one detectable particle.

10. The method of the claim 9 wherein the at least one detectable particle is selected from the group consisting of fluorophores, quantum dots, radioisotopes, and magnetic particles.

* * * * *